(12) United States Patent  
Hu et al.

(10) Patent No.: US 8,143,278 B2
(45) Date of Patent: Mar. 27, 2012

(54) ORGANIC COMPOUNDS

(75) Inventors: Qi-Ying Hu, Needham, MA (US); Gary Michael Ksander, Amherst, NH (US)

(73) Assignee: Novartis AG, Basel (CH)

( * ) Notice: Subject to any disclaimer, the term of this patent is extended or adjusted under 35 U.S.C. 154(b) by 188 days.

(21) Appl. No.: 12/519,703

(22) PCT Filed: Dec. 14, 2007

(86) PCT No.: PCT/US2007/087522
§ 371 (c)(1),
(2), (4) Date: Jun. 17, 2009

(87) PCT Pub. No.: WO2008/076860
PCT Pub. Date: Jun. 26, 2008

(65) Prior Publication Data
US 2010/0093711 A1    Apr. 15, 2010

Related U.S. Application Data

(60) Provisional application No. 60/870,497, filed on Dec. 18, 2006.

(51) Int. Cl.
*C07D 401/02* (2006.01)
*C07D 413/14* (2006.01)
*C07D 417/04* (2006.01)
*A61K 31/4709* (2006.01)

(52) U.S. Cl. ........ 514/312; 514/313; 514/314; 546/158; 546/159

(58) Field of Classification Search .................. 546/158, 546/159; 514/312, 313, 314
See application file for complete search history.

(56) References Cited

U.S. PATENT DOCUMENTS
2009/0105278 A1    4/2009    Hartmann et al.

FOREIGN PATENT DOCUMENTS
EP    0234656    9/1987
WO    2008076336    6/2008
WO    2008076862    6/2008

OTHER PUBLICATIONS

Ulmschneider et al. (2006) "Development and evalutation of a pharmacophore model for inhibitors of aldosterone synthase (CYP11B2)"; Bioorg. Med. Chem. Lett 16: 25-30.
Muller-Vieira et al. (2005) "The adrenocortical tumor cell line NCI-H295R as in in vitro screening system for the evaluation of CYP11B2 (aldosterone synthase) and CYP11B1 (steroid-11 β-hydroxylate) inhibitors"; Journal of Steroid Biochemistry & Molecular Biology 96: 259-270.

*Primary Examiner* — Kahsay T Habte
(74) *Attorney, Agent, or Firm* — Ann R. Pokalsky, Esq; Dilworth & Barrese, LLP

(57) ABSTRACT

The present invention provides a compound of formula I:

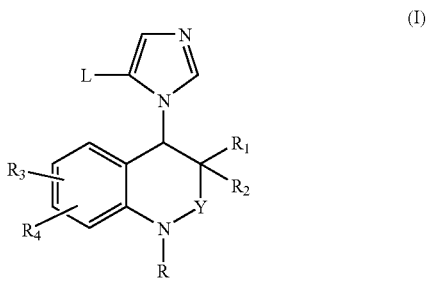

said compound is inhibitor of aldosterone synthase, and/or 11beta-hydroxylase (CYP11B1), and thus can be employed for the treatment of a disorder or disease mediated by aldosterone synthase and/or CYP11B1. Finally, the present invention also provides a pharmaceutical composition.

7 Claims, No Drawings

ORGANIC COMPOUNDS

This application is the National Stage of Application No. PCT/US20071007522, filed on Dec. 14, 2007, which claims benefit under 35 U.S.C. §119(e) of U.S. Provisional Application No. 60/870,497, filed Dec. 18, 2006, the contents of which are incorporated herein by reference in their entirety.

The present invention relates to novel imidazole derivatives that are used as aldosterone synthase inhibitors, and/or 11 beta-hydroxylase inhibitors (CYP11B1), as well as for treatment of a disorder or disease mediated by aldosterone synthase and/or CYP11B1.

The present invention provides a compound of formula (I):

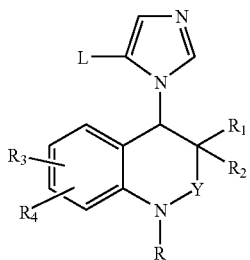

(I)

wherein
Y is —$CH_2$—, —C(O)—, or —$SO_2$—;
L is hydrogen, cyano, halogen, ($C_1$-$C_7$) haloalkyl, ($C_3$-$C_7$) cycloalkyl, ($C_1$-$C_7$) alkyl-O—C(O)—, (5-9)-membered heteroaryl, or ($C_1$-$C_7$) alkyl that is optionally substituted by one or two hydroxyl groups;
$R_1$ and $R_2$ are independently hydrogen or ($C_1$-$C_7$) alkyl; or
$R_1$ and $R_2$ taken together with the carbon atom they are attached to, optionally form a (3-7)-membered ring;
$R_3$ and $R_4$ are independently hydrogen, halogen, ($C_1$-$C_7$) alkoxy or cyano;
R is hydrogen, ($C_1$-$C_7$) alkyl, ($C_1$-$C_7$) haloalkyl, ($C_3$-$C_7$) cycloalkyl, (4-9)-membered heterocyclyl, ($C_5$-$C_{10}$) aryl, ($C_5$-$C_{10}$) aryl-($C_1$-$C_7$) alkyl-, R'—C(O)—, or R'—$SO_2$—, wherein R' is ($C_5$-$C_{10}$) aryl-($C_1$-$C_7$) alkyl-, (4-9)-membered heterocyclyl, or ($C_5$-$C_{10}$) aryl that is optionally substituted by one or two halogen atoms; or
a pharmaceutically acceptable salt thereof; or an optical isomer thereof; or a mixture of optical isomers.

Preferably, the present invention provides the compound of formula (I), wherein Y is —$CH_2$—; L is hydrogen, or ($C_1$-$C_7$) alkyl that is optionally substituted by one or two hydroxyl groups; $R_1$, $R_2$, $R_3$ and $R_4$ are hydrogen; R is hydrogen, ($C_5$-$C_{10}$) aryl, ($C_5$-$C_{10}$) aryl-($C_1$-$C_7$) alkyl-, R'—C(O)—, or R'—$SO_2$—, wherein R' is aryl-alkyl-, (4-9)-membered heterocyclyl, or ($C_5$-$C_{10}$) aryl that is optionally substituted by one or two halogen atoms; or a pharmaceutically acceptable salt thereof; or an optical isomer thereof; or a mixture of optical isomers.

Also preferably, the present invention provides the compound of formula (I), wherein Y is —C(O)—, or —$SO_2$—; L is hydrogen, cyano, halogen, ($C_1$-$C_7$) haloalkyl, ($C_3$-$C_7$) cycloalkyl, ($C_1$-$C_7$) alkyl-O—C(O)—, (5-9)-membered heteroaryl, or ($C_1$-$C_7$) alkyl that is optionally substituted by one or two hydroxyl groups; $R_1$ and $R_2$ are independently hydrogen or ($C_1$-$C_7$) alkyl; $R_3$ and $R_4$ are independently hydrogen, halogen, ($C_1$-$C_7$) alkoxy or cyano; R is hydrogen, ($C_1$-$C_7$) alkyl, ($C_1$-$C_7$) haloalkyl, ($C_3$-$C_7$) cycloalkyl, (4-9)-membered heterocyclyl, ($C_5$-$C_{10}$) aryl, R'—C(O)—, or R'—$SO_2$—, wherein R' is ($C_5$-$C_{10}$) aryl-($C_1$-$C_7$) alkyl-, (5-9)-membered heterocyclyl, or ($C_5$-$C_{10}$) aryl that is optionally substituted by one or two halogen atoms; or a pharmaceutically acceptable salt thereof; or an optical isomer thereof; or a mixture of optical isomers.

Also preferably, the present invention provides the compound of formula (I), wherein Y is —C(O)—, or —$SO_2$—; L is hydrogen, ($C_1$-$C_7$) alkyl-O—C(O)—, or ($C_1$-$C_7$) alkyl that is optionally substituted by one or two hydroxyl groups; $R_1$ and $R_2$ are independently hydrogen or ($C_1$-$C_7$) alkyl; $R_3$ and $R_4$ are independently hydrogen, halogen, ($C_1$-$C_7$) alkoxy; R is hydrogen, ($C_1$-$C_7$) alkyl, ($C_1$-$C_7$) haloalkyl, or ($C_3$-$C_7$) cycloalkyl, (4-9)-membered heterocyclyl; or a pharmaceutically acceptable salt thereof; or an optical isomer thereof; or a mixture of optical isomers.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, heterocyclyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group can be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples of acyl include but are not limited to, acetyl, benzoyl, propionyl, isobutyryl, t-butoxycarbonyl, benzyloxycarbonyl and the like. Lower acyl refers to acyl containing one to four carbons.

As used herein, the term "carbamoyl" refers to $H_2NC(O)$—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—SO$_2$—, wherein R is hydrogen, alkyl, aryl, hereoaryl, aryl-alkyl, heteroaryl-alkyl, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has carbon atoms and at least one heteroatom in at least one carbon atom-containing ring. Each ring of the heterocyclic group containing a heteroatom can have 1, or 2 or 3 heteroatoms selected from nitrogen atoms, oxygen atoms and sulfur atoms, where the nitrogen and sulfur heteroatoms can also optionally be oxidized to various oxidation states. The heterocyclic group can be attached at a heteroatom or a carbon atom. The heterocyclyl can include fused or bridged rings as well as spirocyclic rings.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" further refers to heterocyclic groups as defined herein substituted with 1, 2 or 3 substituents selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(O) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms, preferably 3-9, or 3-7 carbon atoms, each of which can be optionally substituted by one, or two, or three, or more substituents, such as alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to $H_2NS(O)_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, (aryl-alkyl)-NHS(O)$_2$—, (heteroaryl-alkyl)-NHS(O)$_2$— and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2, 3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2, 3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by aldosterone synthase or CYP11B1, or (ii) associated with aldosterone synthase activity or CYP11B1 activity, or (iii) characterized by abnormal activity of aldosterone synthase or CYP11B1; or (2) reducing or inhibiting the activity of aldosterone synthase or CYP11B1; or (3) reducing or inhibiting the expression of aldosterone synthase or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of aldosterone synthase or CYP12B1; or at least partially reducing or inhibiting the expression of aldosterone synthase or CYP11B1. The meaning of the term "a therapeutically effective amount" as illustrated in the above embodiment for aldosterone synthase or CYP11B1 also applies by the same means to any other relevant proteins/peptides/enzymes.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disorder, or disease, or a significant decrease in the baseline activity of a biological activity or process. Preferably, the condition or symptom or disorder or disease is mediated by aldosterone synthase activity or CYP11B1. More preferably, the condition or symptom or disorder or disease is associated with the abnormal activity of aldosterone synthase or CYP11B1, or the condition or symptom or disorder or disease is associated with the abnormal expression of aldosterone synthase or CYP11B1.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "abnormal" refers to an activity or feature which differs from a normal activity or feature.

As used herein, the term "abnormal activity" refers to an activity which differs from the activity of the wild-type or native gene or protein, or which differs from the activity of the gene or protein in a healthy subject. The abnormal activity can be stronger or weaker than the normal activity. In one embodiment, the "abnormal activity" includes the abnormal (either over- or under-) production of mRNA transcribed from a gene. In another embodiment, the "abnormal activity" includes the abnormal (either over- or under-) production of polypeptide from a gene. In another embodiment, the abnormal activity refers to a level of a mRNA or polypeptide that is different from a normal level of said mRNA or polypeptide by about 15%, about 25%, about 35%, about 50%, about 65%, about 85%, about 100% or greater. Preferably, the abnormal level of the mRNA or polypeptide can be either higher or lower than the normal level of said mRNA or polypeptide. Yet in another embodiment, the abnormal activity refers to functional activity of a protein that is different from a normal activity of the wild-type protein. Preferably, the abnormal activity can be stronger or weaker than the normal activity. Preferably, the abnormal activity is due to the mutations in the corresponding gene, and the mutations can be in the coding region of the gene or non-coding regions such as transcriptional promoter regions. The mutations can be substitutions, deletions, insertions.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$)alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656,838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties. The compounds of the present invention are useful as aldosterone synthase inhibitors. Aldosterone synthase (CYP11B2) is a mitcohcondrial cytochrome P450 enzyme catalyzing the last step of aldosterone production in the adrenal cortex, i.e., the conversion of 11-deoxycorticosterone to aldosterone. Aldosterone synthase has been demonstrated to be expressed in all cardiovascular tissues such as heart, umbilical cord, mesenteric and pulmonary arteries, aorta, endothelium and vascular cells. Moreover, the expression of aldosterone synthase is closely correlated with aldosterone production in cells. It has been observed that elevations of aldosterone activities or aldosterone levels induce different diseases such as congestive heart failure, cardiac or myocardial fibrosis, renal failure, hypertension, ventricular arrhythmia and other adverse effects, etc., and that the inhibition of aldosterone or aldosterone synthase would be useful therapeutic approaches. See e.g., Ulmschenider et al. "Development and evaluation of a pharmacophore model for inhibitors of aldosterone synthase (CYP11B2)," *Bioorganic & Medicinal Chemistry Letters*, 16: 25-30 (2006); Bureik et al., "Development of test systems for the discovery of selective human aldosterone synthase (CYP11B2) and 11β-hydroxylase (CYP11B1) inhibitors, discovery of a new lead compound for the therapy of congestive heart failure, myocardial fibrosis and hypertension," *Moleculare and Cellular Endocrinology*, 217: 249-254 (2004); Bos et al., "Inhibition of catechnolamine-induced cardiac fibrosis by an aldosteron antagonist," *J. Cardiovascular Pharmacol*, 45(1): 8-13 (2005); Jaber and Madias, "Progression of chronic kidney disease: can it be prevented or arrested?" *Am. J. Med.* 118(12): 1323-1330 (2005); Khan and Movahed, "The role of aldosterone and aldosterone-receptor antagonists in heart failure," *Rev. Cardiovasc Med.,* 5(2): 71-81 (2004); Struthers, "Aldosterone in heart failure: pathophysiology and treatment," *Cyrr. Heart Fail.,* 1(4): 171-175 (2004); Harris and Rangan, "Retardation of kidney failure—applying principles to practice," *Ann. Acad. Med. Singapore,* 34(1): 16-23 (2005); Arima, "Aldosterone and the kidney: rapid regulation of renal microcirculation," *Steroids*, online publication November 2005; Brown, "Aldosterone and end-organ damage," *Curr. Opin. Nephrol Hypertens,* 14:235-241 (2005); Grandi, "Antihypertensive therapy: role of aldosteron antagonists," *Curr. Pharmaceutical Design,* 11: 2235-2242 (2005); Declayre and Swynghedauw, "Molecular mechanisms of myocardial remodeling: the role of aldosterone," *J. Mol. Cell. Cardiol.,* 34: 1577-1584 (2002). Accordingly, the compounds of the present invention as aldosterone synthase inhibitors, are also useful for treatment of a disorder or disease mediated by aldosterone synthase or responsive to inhibition of aldosterone synthase. In particular, the compounds of the present invention as aldosterone synthase inhibitors are useful for treatment of a disorder or disease characterized by abnormal aldosterone synthase activity. Preferably, the compounds of the present invention are also useful for treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, inflammation, increased formation of collagen, fibrosis such as cardiac or myocardiac fibrosis and remodeling following hypertension and endothelial dysfunction.

Furthermore, the compounds of the present invention are useful as CYP11B1 (11-β-hydroxylase) inhibitors. CYP11B1 catalyzes the last steps of cortisol synthesis. Cortisol is the main glucocorticoid in human. It regulates energy mobilization and thus the stress response. In addition, it is involved in the immune response of the human body. Abnormally increased cortisol level is the cause of a variety of diseases including Cushing's syndrome. Accordingly, the compounds of the present invention as CYP11B1 inhibitors are also useful for the treatment of a disorder or a disease or a condition characterized by abnormal activity or abnormal level of CYP11B1. The compounds of the present invention can be used for the treatment of a disorder, a disease or a condition such as Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

Additionally, the present invention provides:
a compound of the present invention for use as a medicament;
the use of a compound of the present invention for the preparation of a pharmaceutical composition for the delay of progression and/or treatment of a disorder or disease mediated by aldosterone synthase, or characterized by abnormal activity of aldosterone synthase, or by abnormal expression of aldosterone synthase.
the use of a compound of the present invention for the preparation of a pharmaceutical composition for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

Additionally, the present invention provides:

a compound of the present invention for use as a medicament;

the use of a compound of the present invention for the preparation of a pharmaceutical composition for the delay of progression and/or treatment of a disorder or disease or condition mediated by CYP11B1, or characterized by abnormal activity of CYP11B1, or by abnormal expression/level of CYP11B1.

the use of a compound of the present invention for the preparation of a pharmaceutical composition for the delay of progression and/or treatment of a disorder or disease or condition selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The compounds of formula (I) can be prepared by the procedures described in the following sections.

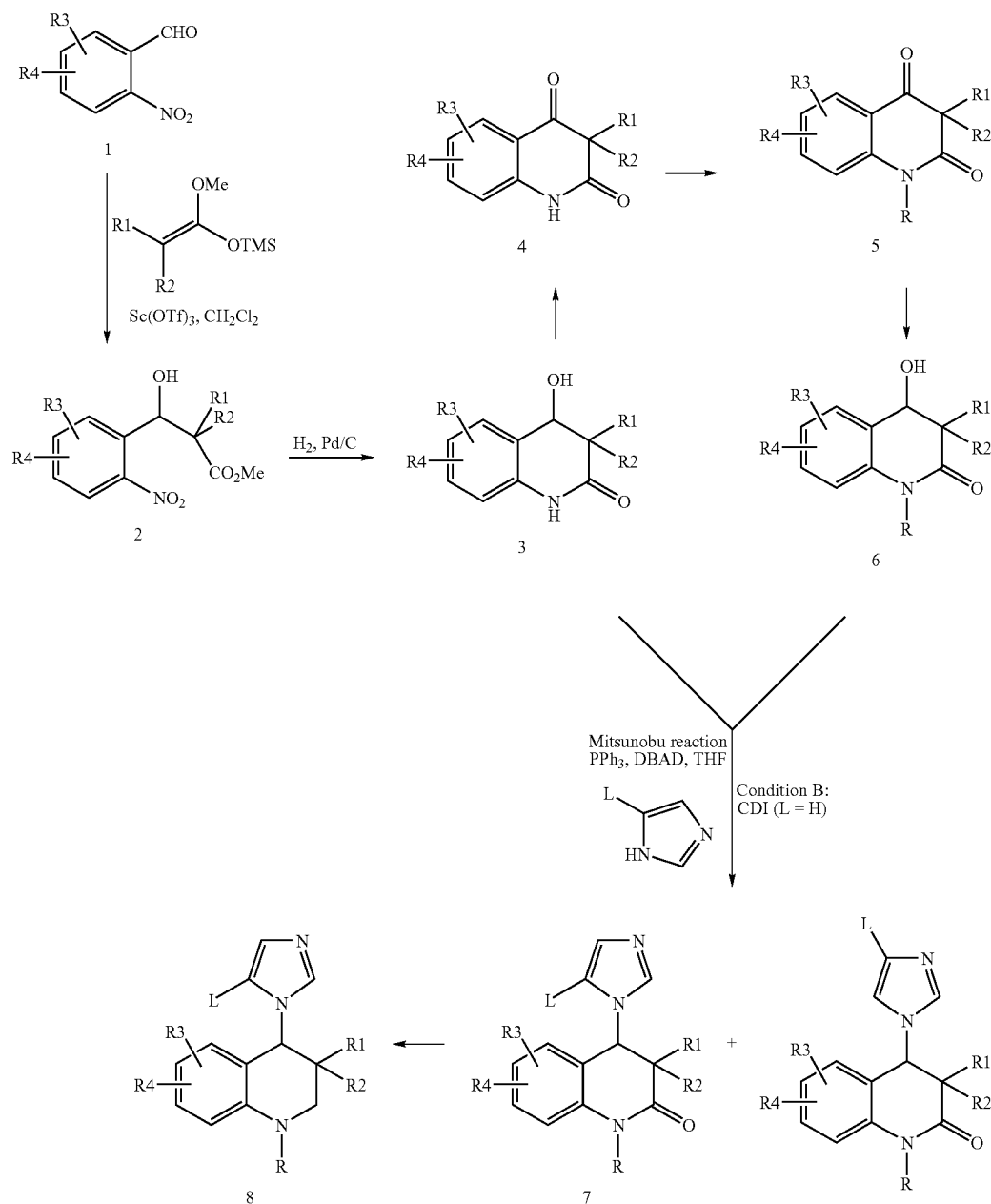

Scheme 1

Two general approaches can be used for the synthesis of (I). The approach A begins with a Lewis acid-catalyzed Mukaiyama aldol reaction of ortho-$NO_2$ substituted aromatic aldehyde (ref. *Synlett* 1993, 472.) to alcohol 2, which can be reduced and simotanously cyclized to the cyclic alcohol 3. Subsequently, the oxidation of alcohol 3 by $MnO2$ to ketone 4, which is reacted with RX (X=suitable leaving group, e.g. Br) in the presence of base (e.g. $K_2CO_3$) to 5. After reduction of 5 by $NaBH4$, the alcohol 6 with N substituted with R is yielded. 3 or 6 can undergo Mitsunobu reaction (ref. *Monastshefte fur Chemie* 2005, 229. *Tetrahedron Lett.* 2005, 631.) with various imidazole to the desired 7 (I). Alternatively, 3 or 6 can react with carbonyl diimidazole to desired 7 (I, L=H) (Ref. *Synthesis* 2004, 2540). The reduction of 7 (I) by $BH3$ can furnish the desired 8 (I, Y=$CH2$).

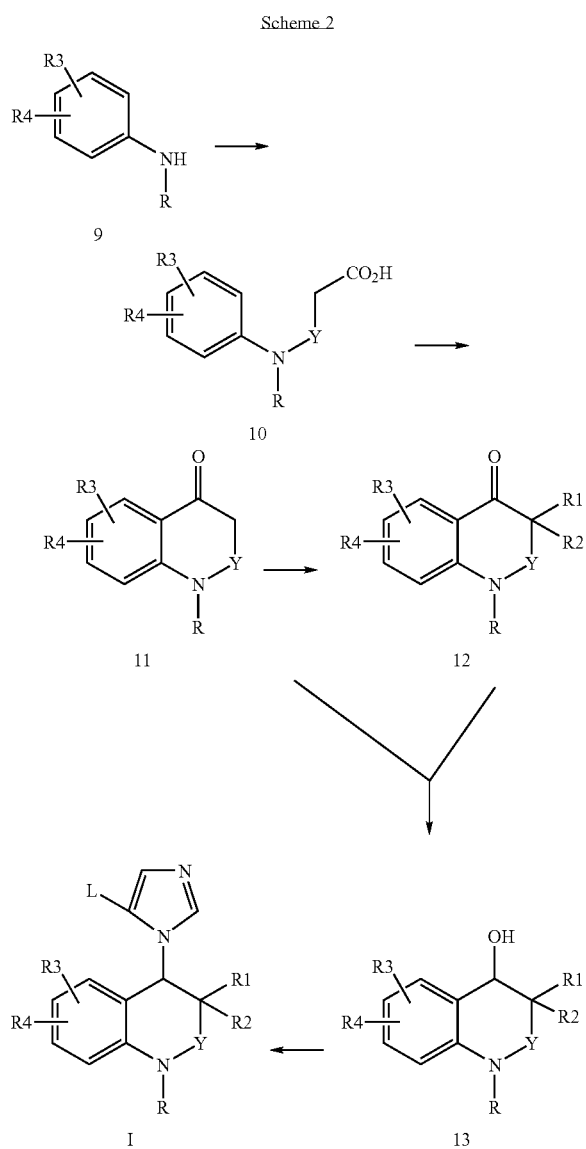

Scheme 2

Alternatively, the synthesis of I can be achieved by the approach described in scheme 2. The synthesis begins with the functionalization of substituted aniline 9 via known protocol (e.g. amide or sulfonamide formation, alkylation et. al.) to the carboxyl derivative 10 which subsequently undergoes a Friedel-Crafts acylation to ketone 11. Alkylation at the α position of ketone 11 provides 12. The subsequent reduction of ketone 11 or 12, yields the benzylic alcohol 13, which can undergo Mitsunobu reaction (ref. *Monastshefte fur Chemie* 2005, 229; *Tetrahedron Lett.* 2005, 631.) with various imidazole to the desired I. Alternatively, 13 can react with carbonyl diimidazole to desired I (L=H) (Ref. *Synthesis* 2004, 2540). Further derivatization to various I can be achieved by known methods, such as reductive amination at N-1, functional group transformation at L, amide or sulfonamide formation at N-1.

Generally, enantiomers of the compounds of the present invention can be prepared by methods known to those skilled in the art to resolve racemic mixtures, such as by formation and recrystallization of diastereomeric salts or by chiral chromotography or HPLC separation utilizing chiral stationery phases.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with one or two or more therapeutic agents, e.g., each at an effective therapeutic dose as reported in the art. Such therapeutic agents include at least one or two or more selected from the following groups:

(i) angiotensin II receptor antagonist or a pharmaceutically acceptable salt thereof,
(ii) HMG-Co-A reductase inhibitor or a pharmaceutically acceptable salt thereof,
(iii) angiotensin converting enzyme (ACE) Inhibitor or a pharmaceutically acceptable salt thereof,
(iv) calcium channel blocker (CCB) or a pharmaceutically acceptable salt thereof,
(v) dual angiotensin converting enzyme/neutral endopeptidase (ACE/NEP) inhibitor or a pharmaceutically acceptable salt thereof,
(vi) endothelin antagonist or a pharmaceutically acceptable salt thereof,
(vii) renin inhibitor or a pharmaceutically acceptable salt thereof,
(viii) diuretic or a pharmaceutically acceptable salt thereof,
(ix) an ApoA-I mimic;
(x) an anti-diabetic agent;
(xi) an obesity-reducing agent;
(xii) an aldosterone receptor blocker;
(xiii) an endothelin receptor blocker;
(xiv) a CETP inhibitor;
(xv) an inhibitor of Na-K-ATPase membrane pump;
(xvi) a beta-adrenergic receptor blocker or an alpha-adrenergic receptor blocker;
(xvii) a neutral endopeptidase (NEP) inhibitor; and
(xviii) an inotropic agent.

An angiotensin II receptor antagonist or a pharmaceutically acceptable salt thereof is understood to be an active ingredients which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

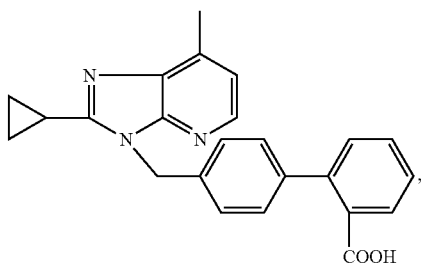

the compound with the designation SC-52458 of the following formula

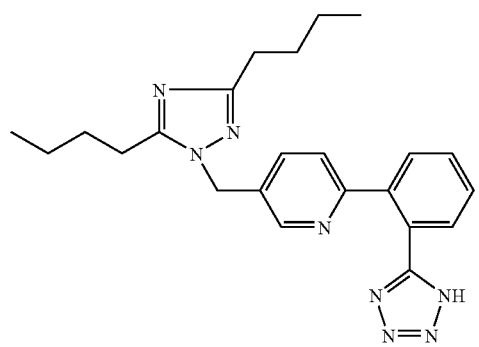

and the compound with the designation ZD-8731 of the following formula

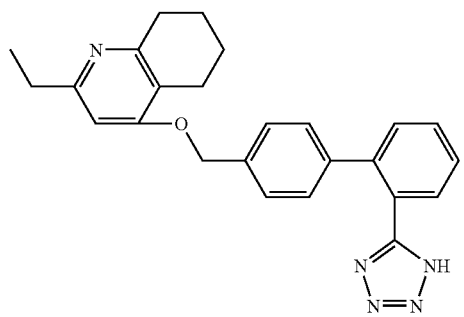

or, in each case, a pharmaceutically acceptable salt thereof.

Preferred $AT_1$-receptor antagonist are those agents which have been marketed, most preferred is valsartan or a pharmaceutically acceptable salt thereof.

HMG-Co-A reductase inhibitors (also called beta-hydroxy-beta-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, such as atorvastatin, fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

Suitable renin inhibitors include compounds having different structural features. For example, mention may be made of compounds which are selected from the group consisting of ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmrthyl)amino]carbonyl]butyl]amino] carbonyl]hexyl]-N-alfa-methyl-L-histidinamide); terlakiren (chemical name: [R—(R*,S*)]—N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl] methyl]-1-oxo-3-phenylpropyl]-amino]-4-thiazolepropanamide), preferably, in each case, the hydrochloride salt thereof, SPP630, SPP635 and SPP800 as developed by Speedel.

Preferred renin inhibitor of the present invention include RO 66-1132 and RO 66-1168 of formula (A) and (B)

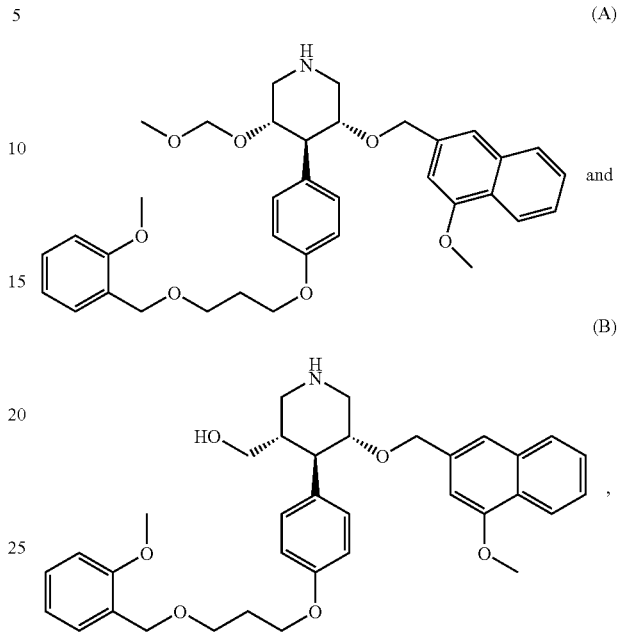

respectively, or a pharmaceutically acceptable salt thereof.

In particular, the present invention relates to a renin inhibitor which is a δ-amino-γ-hydroxy-ω-aryl-alkanoic acid amide derivative of the formula (C)

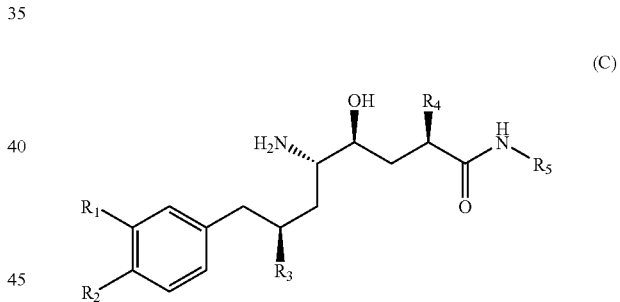

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$alkoxy-$C_{1-6}$alkyl, $C_{1-6}$alkanoyloxy-$C_{1-6}$alkyl, $C_{1-6}$-aminoalkyl, $C_{1-6}$alkylamino-$C_{1-6}$alkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}$alkyl$)_2$N—C(O)—$C_{1-6}$alkyl; or a pharmaceutically acceptable salt thereof.

As an alkyl, $R_1$ may be linear or branched and preferably comprise 1 to 6 C atoms, especially 1 or 4 C atoms. Examples are methyl, ethyl, n- and i-propyl, n-, i- and t-butyl, pentyl and hexyl.

As a halogenalkyl, $R_1$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

As a $C_{1-6}$alkoxy-$C_{1-6}$alkyloxy, $R_1$ may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethoxyhexyloxy, propyloxymethyloxy, butyloxymethyloxy, 2-propyloxyethyloxy and 2-butyloxyethyloxy.

In a preferred embodiment, $R_1$ is methoxy- or ethoxy-$C_{1-4}$alkyloxy, and $R_2$ is preferably methoxy or ethoxy. Particularly preferred are compounds of formula (III), wherein $R_1$ is 3-methoxypropyloxy and $R_2$ is methoxy.

As a branched alkyl, $R_3$ and $R_4$ preferably comprise 3 to 6 C atoms. Examples are i-propyl, i- and t-butyl, and branched isomers of pentyl and hexyl. In a preferred embodiment, $R_3$ and $R_4$ in compounds of formula (C) are in each case i-propyl.

As a cycloalkyl, $R_5$ may preferably comprise 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro, cyano, heterocyclyl and the like.

As an alkyl, $R_5$ may be linear or branched in the form of alkyl and preferably comprise 1 to 6 C atoms. Examples of alkyl are listed herein above. Methyl, ethyl, n- and i-propyl, n-, i- and t-butyl are preferred.

As a $C_{1-6}$hydroxyalkyl, $R_5$ may be linear or branched and preferably comprise 2 to 6 C atoms. Some examples are 2-hydroxyethyl, 2-hydroxypropyl, 3-hydroxypropyl, 2-, 3- or 4-hydroxybutyl, hydroxypentyl and hydroxyhexyl.

As a $C_{1-6}$alkoxy-$C_{1-6}$alkyl, $R_5$ may be linear or branched. The alkoxy group preferably comprises 1 to 4 C atoms and the alkyl group preferably 2 to 4 C atoms. Some examples are 2-methoxyethyl, 2-methoxypropyl, 3-methoxypropyl, 2-, 3- or 4-methoxybutyl, 2-ethoxyethyl, 2-ethoxypropyl, 3-ethoxypropyl, and 2-, 3- or 4-ethoxybutyl.

As a $C_{1-6}$alkanoyloxy-$C_{1-6}$alkyl, $R_5$ may be linear or branched. The alkanoyloxy group preferably comprises 1 to 4 C atoms and the alkyl group preferably 2 to 4 C atoms. Some examples are formyloxymethyl, formyloxyethyl, acetyloxyethyl, propionyloxyethyl and butyroyloxyethyl.

As a $C_{1-6}$aminoalkyl, $R_5$ may be linear or branched and preferably comprise 2 to 4 C atoms. Some examples are 2-aminoethyl, 2- or 3-aminopropyl and 2-, 3- or 4-aminobutyl.

As $C_{1-6}$alkylamino-$C_{1-6}$alkyl and $C_{1-6}$dialkylamino-$C_{1-6}$alkyl, $R_5$ may be linear or branched. The alkylamino group preferably comprises $C_{1-4}$alkyl groups and the alkyl group has preferably 2 to 4 C atoms. Some examples are 2-methylaminoethyl, 2-dimethylaminoethyl, 2-ethylaminoethyl, 2-ethylaminoethyl, 3-methylaminopropyl, 3-dimethylaminopropyl, 4-methylaminobutyl and 4-dimethylaminobutyl.

As a HO(O)C—$C_{1-6}$alkyl, $R_5$ may be linear or branched and the alkyl group preferably comprises 2 to 4 C atoms. Some examples are carboxymethyl, carboxyethyl, carboxypropyl and carboxybutyl.

As a $C_{1-6}$alkyl-O—(O)C—$C_{1-6}$alkyl, $R_5$ may be linear or branched, and the alkyl groups preferably comprise independently of one another 1 to 4 C atoms. Some examples are methoxycarbonylmethyl, 2-methoxycarbonylethyl, 3-methoxycarbonylpropyl, 4-methoxy-carbonylbutyl, ethoxycarbonylmethyl, 2-ethoxycarbonylethyl, 3-ethoxycarbonylpropyl, and 4-ethoxycarbonylbutyl.

As a $H_2N$—C(O)—$C_{1-6}$alkyl, $R_5$ may be linear or branched, and the alkyl group preferably comprises 2 to 6 C atoms. Some examples are carbamidomethyl, 2-carbamidoethyl, 2-carbamido-2,2-dimethylethyl, 2- or 3-carbamidopropyl, 2-, 3- or 4-carbamidobutyl, 3-carbamido-2-methylpropyl, 3-carbamido-1,2-dimethylpropyl, 3-carbamido-3-ethylpropyl, 3-carbamido-2,2-dimethylpropyl, 2-, 3-, 4- or 5-carbamidopentyl, 4-carbamido-3,3- or -2,2-dimethylbutyl. Preferably, $R_5$ is 2-carbamido-2,2-dimethylethyl.

Accordingly, preferred are δ-amino-γ-hydroxy-ω-aryl-alkanoic acid amide derivatives of formula (C) having the formula

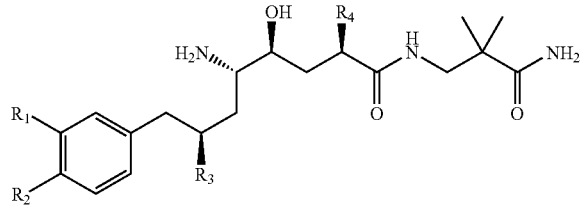

(D)

wherein $R_1$ is 3-methoxypropyloxy; $R_2$ is methoxy; and $R_3$ and $R_4$ are isopropyl; or a pharmaceutically acceptable salt thereof; chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide, also known as aliskiren.

The term "aliskiren", if not defined specifically, is to be understood both as the free base and as a salt thereof, especially a pharmaceutically acceptable salt thereof, most preferably a hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-I mimic is, for example, D4F peptide, especially of formula D-W-F-K-A-F-Y-D-K-V-A-E-K-F-K-E-A-F An anti-diabetic agents include insulin secretion enhancers which are active ingredients that have the property to promote the secretion of insulin from pancreatic β-cells. Examples of insulin secretion enhancers are a biguanide derivative, for example, metformin or, if appropriate, a pharmaceutically acceptable salt thereof, especially the hydrochloride thereof. Other insulin secretion enhancers include sulfonylureas (SU), especially those which promote the secretion of insulin from pancreatic β-cells by transmitting signals of insulin secretion via SU receptors in the cell membrane, including (but are not limited to) tolbutamide; chlorpropamide; tolazamide; acetohexamide; 4-chloro-N-[(1-pyrrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or pharmaceutically acceptable salts thereof.

Insulin secretion enhancers furthermore include short-acting insulin secretion enhancers, such as the phenylalanine derivative nateglinide [N-(trans-4-isopropylcyclohexyl-carbonyl)-D-phenylalanine] (cf. EP 196222 and EP 526171) of the formula

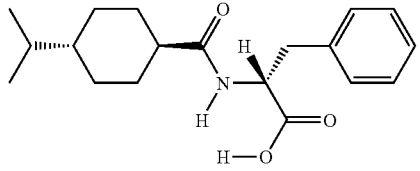

and repaglinide [(S)-2-ethoxy-4-{2-[[3-methyl-1-[2-(1-piperidinyl)phenyl]butyl]amino]-2-oxoethyl}benzoic acid]. Repaglinide is disclosed in EP 589874, EP 147850 A2, in particular Example 11 on page 61, and EP 207331 A1. It can be administered in the form as it is marketed, e.g. under the trademark NovoNorm™; calcium (2S)-2-benzyl-3-(cis-hexahydro-2-isoindolinlycarbonyl)-propionate dihydrate (mitiglinide cf. EP 507534); furthermore representatives of the new generation of SUs such as glimepiride (cf. EP 31058); in free or pharmaceutically acceptable salt form. The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 of said U.S. patent (referring to H-form crystal modification) as well as the corresponding references to the B-type crystal modification in EP 196222 B1 the subject matter of which, especially with respect to the identification, manufacture and characterization of the B-form crystal modification. Preferably, in the present invention, the B- or H-type, more preferably the H-type, is used. Nateglinide can be administered in the form as it is marketed e.g. under the trademark STARLIX™.

Insulin secretion enhancers likewise include the long-acting insulin secretion enhancer DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is a insulinotropic protein which was described, e.g., by W. E. Schmidt et al. in *Diabetologia*, 28, 1985, 704-707 and in U.S. Pat. No. 5,705,483.

The term "GLP-1 agonists" used herein means variants and analogs of GLP-1(7-36)$NH_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. The term "GLP-1 agonists" comprises especially compounds like GLP-1(7-37), in which compound the carboxy-terminal amide functionality of $Arg^{36}$ is displaced with Gly at the $37^{th}$ position of the GLP-1(7-36) $NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1 (7-37)OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al in Diabetologia 1999, 42, 45-50.

An insulin sensitivity enhancer restores impaired insulin receptor function to reduce insulin resistance and consequently enhance the insulin sensitivity.

An appropriate insulin sensitivity enhancer is, for example, an appropriate hypoglycemic thiazolidinedione derivative (glitazone).

An appropriate glitazone is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methylcyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{-4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{-4-[2-(5-methyl-2-phenyl-4-oxazolyl)-2-hydroxyethoxy]benzyly}thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl]-2-propynyl]-5-(4-fluorophenyl-sulfonyl)thiazolidine-2,4-dione, 5-{[4-(2-(methyl-2-pyridinyl-amino)-ethoxy)phenyl]methyl}thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297). Preferred are pioglitazone, rosiglitazone and troglitazone.

Other anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6 Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; and $\alpha_2$-adrenergic antagonists; in which the active ingredients are present in each case in free form or in the form of a pharmaceutically acceptable salt.

An obesity-reducing agent includes lipase inhibitors such as orlistat and appetite suppressants such as sibutramine, phentermine.

An aldosteron receptor blocker includes spironolactone and eplerenone.

An endothelin receptor blocker includes bosentan, etc.

A CETP inhibitor refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). The CETP inhibitors include those disclosed in U.S. Pat. Nos. 6,140,343 and 6,197,786. CETP inhibitors disclosed in these patents include compounds, such as [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol. CETP inhibitors also include those described in U.S. patent application Ser. No. 10/807,838 filed Mar. 23, 2004. U.S. Pat. No. 5,512,548 discloses certain polypeptide derivatives having activity as CETP inhibitors, also certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.;* 6:1951-1954 (1996), respectively. Furthermore, the CETP inhibitors also include those disclosed in WO2000/017165, WO2005/095409 and WO2005/097806.

A Na_K-ATPase inhibitor can be used to inhibit the Na and K exchange across the cell membranes. Such inhibitor can be for example digoxin.

A beta-adrenergic receptor blocker includes but is not limited to: esmolol especially the hydrochloride thereof; acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. Nos. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol; which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., *Journal of Medicinal Chemistry*, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

An alpha-adrenergic receptor blocker includes but is not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The natriuretic peptides constitute a family of peptides that include the atrial (ANP), brain-derived (BNP) and C-type natriuretic (CNP) peptides. The natriuretic peptides effect vasodilation, natriuresis, diuresis, decreased aldosterone release, decreased cell growth, and inhibition of the sympathetic nervous system and the renin-angiotensin-aldosterone system indicating their involvement in the regulation of blood pressure and of sodium and water balance. Neutral endopeptidase 24. 11 (NEP) inhibitors impede degradation of natriuretic peptides and elicit pharmacological actions potentially beneficial in the management of several cardiovascular disorders. A NEP inhibitor useful in the said combination is an agent selected from the group represented by candoxatril, sinorphan, SCH 34826 and SCH 42495.

An inotropic agent is selected from the group consisting of: digoxin, digitoxin, digitalis, dobutamine, dopamine, epinephrine, milrinone, amrinone and norepinephrine, etc.

A compound of the present invention may be administered either simultaneously, before or after the other active ingredient, either separately by the same or different route of administration or together in the same pharmaceutical formulation.

Furthermore, the combinations as described above can be administered to a subject via simultaneous, separate or sequential administration (use). Simultaneous administration (use) can take place in the form of one fixed combination with two or three or more active ingredients, or by simultaneously administering two or three or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two, or three or more compounds are administered such that no overlap of measurable blood levels of both compounds are present in an overlapping manner (at the same time).

Also combinations of two or three or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Alternatively, the pharmaceutical compositions contain a therapeutically effective amount of a compound of the invention as defined above, either alone or in a combination with one or more therapeutic agents, e.g., each at an effective therapeutic dose as reported in the art, selected from the group consisting of an antiestrogen; an anti-androgen; a gonadorelin agonist; a topoisomerase I inhibitor; a topoisomerase II inhibitor; a microtubule active agent; an alkylating agent; an anti-neoplastic anti-metabolite; a platin compound; a compound targeting/decreasing a protein or lipid kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier; an inhibitor of Ras oncogenic isoforms; a telomerase inhibitor; a protease inhibitor, a matrix metalloproteinase inhibitor, a methionine aminopeptidase inhibitor; a proteasome inhibitor; agents which target, decrease or inhibit the activity of Flt-3; an HSP90 inhibitor; antiproliferative antibodies; an HDAC inhibitor; a compound which targets, decreases or inhibits the activity/function of serine/theronine mTOR kinase; a somatostatin receptor antagonist; an anti-leukemic compound; tumor cell damaging approaches; an EDG binder; a ribonucleotide reductase inhibitor; an S-adenosylmethionine decarboxylase inhibitor; a monoclonal antibody of VEGF or VEGFR; photodynamic therapy; an Angiostatic steroid; an implant containing corticosteroids; an AT1 receptor antagonist; and an ACE inhibitor.

Additionally, the present invention provides:
a pharmaceutical composition or combination of the present invention for use as a medicament;
the use of a pharmaceutical composition or combination of the present invention for the delay of progression and/or treatment of a disorder or disease mediated by or associated with aldosterone synthase, or responsive to inhibition of aldosterone synthase, or characterized by abnormal activity or expression of aldosterone synthase.
the use of a pharmaceutical composition or combination of the present invention for the delay of progression and/or treatment of a disorder or disease mediated by or associated with CYP11B1, or responsive to inhibition of CYP11B1, or characterized by abnormal activity or expression of CYP11B1.
the use of a pharmaceutical composition or combination of the present invention for the delay of progression and/or treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardial fibrosis and remodeling following hypertension and endothelial dysfunction.
the use of a pharmaceutical composition or combination of the present invention for the delay of progression and/or treatment of a disorder or disease selected from Cushing's syndrome, diseases or disorders due to excessive CYP11B1 level, the ectopic ACTH syndrome, the change in adrenocortical mass, primary pigmented nodular adrenocortical disease (PPNAD), Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The pharmaceutical composition or combination of the present invention can be in unit dosage of about 1-1000 mg of active ingredients for a subject of about 50-70 kg, preferably about 1-500 mg or about 1-250 mg or about 1-150 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The activities of a compound according to the present invention can be assessed by the following in vitro & in vivo methods well-described in the art. See Fieber, A et al. (2005), "Aldosterone Synthase Inhibitor Ameliorates Angiotensin II-Induced Organ Damage," *Circulation*, 111:3087-3094. The reference cited herein is incorporated by reference in its entirety.

In particular, the aldosterone synthase inhibitory activities in vitro can be determined by the following assays.

Human adrenocortical carcinoma NCI-H295R cell line is obtained from American Type Culture Collection (Manassas, Va.). Insulin/transferrin/selenium (ITS)-A supplement (100×), DMEM/F-12, antibiotic/antimycotic (100×), and fetal calf serum (FCS) are purchased from Gibco (Grand Island, N.Y.). Anti-mouse PVT scintillation proximity assay (SPA) beads and NBS 96-well plates are obtained from Amersham (Piscataway, N.J.) and Corning (Acton, Mass.), respectively. Solid black 96-well flat bottom plates are purchased from Costar (Corning, N.Y.). Aldosterone and angiotensin (Ang II) are purchased from Sigma (St. Louis, Mo.). D[1,2,6,7-$^3$H(N)]aldosterone was acquired from PerkinElmer (Boston, Mass.). Nu-serum was a product of BD Biosciences (Franklin Lakes, N.J.). The NADPH regenerating system, dibenzylfluorescein (DBF), and human aromatase Supersomes® are obtained from Gentest (Woburn, Mass.).

For in vitro measurement of aldosterone activity, human adrenocortical carcinoma NCI-H295R cells are seeded in NBS 96-well plates at a density of 25,000 cells/well in 100 µl of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 µl of DMEM/F12 and incubated with 100 µl of treatment medium containing 1 µM Ang II and a compound at different concentrations in quadruplicate wells at 37° C. for 24 hr. At the end of incubation, 50 µl of medium is withdrawn from each well for measurement of aldosterone production by an RIA using mouse anti-aldosterone monoclonal antibodies.

Measurement of aldosterone activity can also be performed using a 96-well plate format. Each test sample is incubated with 0.02 µCi of D-[1,2,6,7-$^3$H(N)]aldosterone and 0.3 µg of anti-aldosterone antibody in phosphate-buffered saline (PBS) containing 0.1% Triton X-100, 0.1% bovine serum albumin, and 12%, glycerol in a total volume of 200 µl at room temperature for 1 hr. Anti-mouse PVT SPA beads (50 µl) are then added to each well and incubated overnight at room temperature prior to counting in a Microbeta plate counter. The amount of aldosterone in each sample is calculated by comparing with a standard curve generated using known quantities of the hormone.

Full concentration-response curves of the test compound are performed at least 3 times. The $IC_{50}$ values are derived using a non-linear least squares curve-fitting program from Microsoft XLfit.

The in vivo inhibitory activities for aldosterone synthase can be determined by the following assays.

Test compounds (I.e., potential aldosterone synthase inhibitors) are profiled in vivo in a conscious rat model of acute secondary hyperaldosteronism. Wild-type rats are instrumented with chronically indwelling arterial and venous cannulas, which are exteriorized through a tether/swivel system. The ambulatory rats are housed in specialized cages to allow blood sampling and parenteral drug administration without disturbing the animals. Angiotensin II is continuously infused intravenously at a level sufficient to elevate plasma aldosterone concentration (PAC) by ~200-fold to 1-5 nM. This PAC increase is sustained at a stable level for at least 8-9 hours. Test compounds are administered p.o. (via oral gavage) or parenterally (via the arterial catheter) after one hour of angiotensin II infusion at a time when PAC has increased to a steady-state level. Arterial blood samples are collected before and at various times (up to 24 hours) after test agent administration for later determination of PAC and concentration of test agent. From these measurements, various parameters can be derived, e.g., 1) onset and duration of PAC reduction by the test agent, 2) pharmacokinetic parameters of the test agent such as half-life, clearance, volume of distribution, and oral bioavailability, 3) dose/PAC response, dose/test-agent concentration, and test-agent concentration/PAC response relationships, and 4) dose- and concentration-potencies and efficacy of the test agent. A successful test compound decreases PAC in a dose- and time-dependent fashion in the dose range of about 0.01 to about 10 mg/kg i.a. or p.o.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have CYP11B1 (steroid 11 p-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been I supplemented with Ulroser SF Serum (Soprachem, Cergy-Saint-Christophe, France), insulin, transferrin, selenite (I-T-S, Becton Dickinson Biosiences, Franklin lakes, NJ, USA) and antibiotics in 75 $cm^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin 11 (1 D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$ I where: a=minimum data level b=gradient I c=ICED d=maximum data level x=inhibitor concentration.

TABLE 1

Inhibitory Activity of Compounds

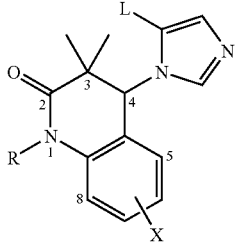

| # | Isomeric | X | R | L | ASI cell IC50 (nM) | % inhibition CYP11B1 @ 10 nM |
|---|---|---|---|---|---|---|
| 1 | R | H | H | —CO$_2$CH$_3$ | 11 | 80 |
| 2 | R | H | CH$_3$ | —CO$_2$CH$_3$ | 10 | 61 |
| 3 | R | H | H | —CH$_2$OH | 40 | 53 |
| 4 | Ent-1 | H | H | —CH$_2$OH | 129 | 23 |
| 5 | Ent-2 | H | H | —CH$_2$OH | 7 | 72 |
| 6 | R | 7-OCH$_3$ | H | H | 34 | 84 |
| 7 | R | H | CH$_3$ | H | 10 | 100 |
| 8 | R | 5-Cl | H | —CH$_2$OH | 7 | |
| 9 | R | 7-F | H | CH$_3$ | 12 | |
| 10 | R | H | H |  | 137 | |

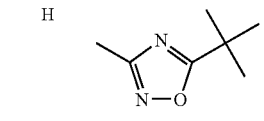

| 1 | R | H | H | —CH$_2$OH | 5 | 93 |
| 2 | Ent-1 | H | H | —CH$_2$OH | 4 | 96 |
| 3 | Ent-1 | H | —SO$_2$Ph | —CO$_2$CH$_3$ | 8 | |
| 4 | R | H | —CH$_2$Ph | —CH$_2$OH | 6 | |
| 5 | R | H | CH$_3$ | —CH$_2$OH | 28 | |

Ent-1: the first eluting enantiomer.
R: racemic.
Ph: phenyl.
Ent-2: the second eluting enantiomer.
AS: aldosterone synthase;
ARO: Aromatase;
11B1: CYP11B1;
I % percentage of inhibitory rate.

ABBREVIATIONS

CDI: carbonyl diimidazole
DBAD: di-tert-butyl azodicarboxylate
DCM: dichloromethane
DIBAL: diisobutylaluminum hydride
DMAP: N,N-dimethylaminopyridine
DME: dimethoxyethane
DMF: N, N-dimethylformamide
DMSO: dimethylsulfoxide
ESI: electrospray ionization
h: hours
HPLC: high pressure liquid chromatography
HRMS: high resolution mass spectrometry
IPA/i-PrOH: iso-propyl alcohol
IR: infrared spectroscopy
LAH: lithium aluminum hydride
LCMS: liquid chromatography/mass spectrometry
LDA: lithium diisoproylamide
LHMDS/LiHMDS: lithium hexamethyldisilazide
min: minutes
MS: mass spectrometry
NBS: N-bromosuccinimide
NMR: nuclear magnetic resonance
TBSCl: tert-butyldimethylsilyl chloride
TFA: trifluoroacetic acid
THF: tetrahydrofuran
TMEDA: tetramethylethylenediannine
TBS: tert-butyl dimethylsilyl
TBDPSCl: tert-butyldiphenylsilyl chloride
TBDPS: tert-butyldiphenylsilyl
TMSCl: trimethylsilyl chloride
TLC: thin layer chromatography
Tr: trityl
$t_r$: retention time

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the following examples have been found to have IC$_{50}$ values in the range of about 0.1 nM to about 100,0.00 nM for aldosterone synthase.

Example 1

3-(3,3-Dimethyl-2-oxo-1,2,3,4-tetrahydro-quinolin-4-yl)-3H-imidazole-4-carboxylic acid methyl ester. & 1-(3,3-Dimethyl-2-oxo-1,2,3,4-tetrahydro-quinolin-4-yl)-1H-imidazole-4-carboxylic acid methyl ester

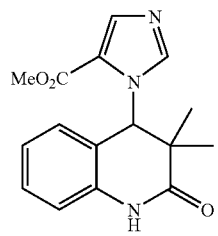

Step A. Synthesis of 3-Hydroxy-2,2-dimethyl-3-(2-nitro-phenyl)-propionic acid methyl ester

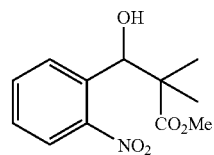

1-Methoxy-1-(trimethylsiloxy)-2-methyl-1-propene (2.4 mL, 2.092 g, 12 mmol) is added dropwise to a suspension of 2-Nitro-benzaldehyde (1.51 g, 10 mmol), Scandium (III) trifluoromethanesulfonate (148 mg, 0.3 mmol) in 30 mL of dry CH$_2$Cl$_2$ at −78° C. The resulting mixture is slowly warmed up to 0° C. and stirred for 1 h. The reaction is quenched with 1 M HCl and stirred for 1 h at room temperature. After extraction with ethyl acetate (20 mL×3), washed with brine, dried over anhydrous Na$_2$SO$_4$ and concentration, the residue is purified by flash column, and gives a yellow oil (800 mg).

Step B. 4-Hydroxy-3,3-dimethyl-3,4-dihydro-1H-quinolin-2-one

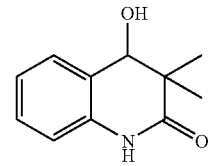

A mixture of 3-Hydroxy-2,2-dimethyl-3-(2-nitro-phenyl)-propionic acid methyl ester (800 mg), Palladium on carbon (10%, 80 mg) in 5 mL of MeOH under 1 atm hydrogen gas is stirred at room temperature for 4 h. The mixture is filtered through a pad of celite and washed with MeOH. The combined solution is concentrated and the residue is purified by flash column and gives 250 mg colorless solid.

The following intermediates can be prepared by similar procedure.

6-Fluoro-4-hydroxy-3,3-dimethyl-3,4-dihydro-1H-quinolin-2-one

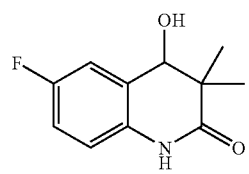

7-Methoxy-4-hydroxy-3,3-dimethyl-3,4-dihydro-1H-quinolin-2-one

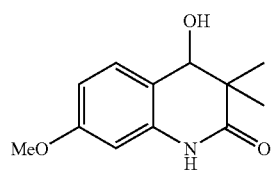

5-Chloro-4-hydroxy-3,3-dimethyl-3,4-dihydro-1H-quinolin-2-one

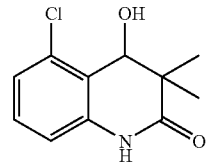

7-Fluoro-4-hydroxy-3,3-dimethyl-3,4-dihydro-1H-quinolin-2-one

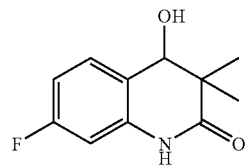

Step C. 3-(3,3-Dimethyl-2-oxo-1,2,3,4-tetrahydro-quinolin-4-yl)-3H-imidazole-4-carboxylic acid methyl ester

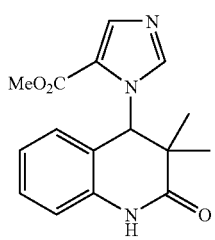

and 1-(3,3-Dimethyl-2-oxo-1,2,3,4-tetrahydro-quinolin-4-yl)-1H-imidazole-4-carboxylic acid methyl ester

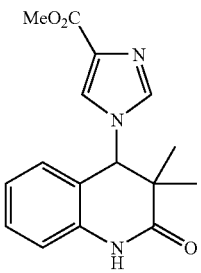

A solution of di-butyl azodicarboxylate (145 mg, 0.6275 mmol) in 2 mL of dry THF is added dropwise to a suspension of 3H-Imidazole-4-carboxylic acid methyl ester (79 mg, 0.6275 mmol), PPh$_3$ (165 mg, 0.6275 mmol), and 4-Hydroxy-3,3-dimethyl-3,4-dihydro-1H-quinolin-2-one (80 mg, 0.418 mg) in 3 mL of dry THF at 0° C. The resulting mixture is slowly warmed up to room temperature, and stirred for 2 h. The reaction is quenched with 2 M HCl and stirred for another 0.5 h. After concentration, the residue is dissolved in HCl (2 M) and extracted with ethyl acetate (20 mL×3). The aqueous layer is adjusted to pH 8-9 by addition of saturated NaHCO$_3$ solution. Subsequently, the mixture is extracted with ethyl acetate (20 mL×3). The combined extracts are washed with brine, and dried over anhydrous Na$_2$SO$_4$. After concentration, the residue is purified by flash column first then by reverse phase HPLC and gives two title regioisomers.

3-(3,3-Dimethyl-2-oxo-1,2,3,4-tetrahydro-quinolin-4-yl)-3H-imidazole-4-carboxylic acid methyl ester: $^1$H NMR (400.3 MHz, CDCl$_3$): δ 8.28 (brs, 1H), 7.67 (s, 1H), 7.45 (s, 1H), 7.28-7.22 (m, 2H), 6.97 (t, J=8.0 Hz, 1H), 6.83 (d, J=8.0 Hz, 1H), 6.42 (s, 1H), 3.85 (s, 3H), 1.26 (s, 3H), 1.02 (s, 3H). HRMS: calculated for C$_{16}$H$_{18}$N$_3$O$_3$: 300.1348. Found: 300.1354.

1-(3,3-Dimethyl-2-oxo-1,2,3,4-tetrahydro-quinolin-4-yl)-1H-imidazole-4-carboxylic acid methyl ester. $^1$H NMR (400.3 MHz, CDCl$_3$): δ 8.25 (brs, 1H), 7.48 (s, 1H), 7.43 (s, 1H), 7.31-7.27 (m, 1H), 7.11 (d, J=8.0 Hz, 1H), 7.00 (t, J=8.0 Hz, 1H), 6.87 (d, J=8.0 Hz, 1H), 4.90 (s, 1H), 3.78 (s, 3H), 1.24 (s, 3H), 1.07 (s, 3H). HRMS (ESI): calculated for C$_{16}$H$_{18}$N$_3$O$_3$: 300.1348. Found: 300.1351.

Resolution of 3-(3,3-Dimethyl-2-oxo-1,2,3,4-tetrahydro-quinolin-4-yl)-3H-imidazole-4-carboxylic acid methyl ester is achieved by chiral HPLC using the ChiralPak AS-H column with a 10% EtOH/Hexanes as mobile phase to give enantiomers with retention time t$_r$=15.3 min and t$_r$=18.3 min.

The following compounds can be prepared by employing similar procedure.

3-(3,3-Dimethyl-2-oxo-1,2,3,4-tetrahydro-quinolin-4-yl)-3H-imidazole-4-carboxylic acid ethyl ester

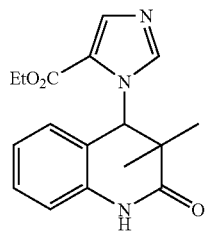

$^1$H NMR (400.3 MHz, DMSO-d6): δ 10.60 (s, 1H), 7.68 (s, 1H), 7.47 (s, 1H), 7.35 (t, J=8 Hz, 1H), 7.25 (d, J=4.0 Hz, 1H), 7.07-6.99 (m, 2H), 6.30 (s, 1H), 4.35 (q, J=8.0 Hz, 2H), 1.33 (t, J=8.0 Hz, 3H), 1.16 (s, 3H), 0.87 (s, 3H). $^{13}$C NMR (100.6 MHz, DMSO-d6): δ 172.42, 160.27, 139.68, 137.26, 136.58, 130.04, 129.14, 123.06, 122.37, 120.75, 115.89, 60.55, 59.53, 42.65, 24.77, 18.97, 14.09. HRMS (ESI): calculated for C$_{17}$H$_{19}$N$_3$O$_3$: 314.1505 Found: 314.1497. Resolution of the enantiomers is achieved by chiral HPLC using the ChiralPak IA column with a 25% EtOH/Heptane as mobile phase to give enantiomers with retention time t$_r$=18 min and t$_r$=26 min.

1-(3,3-Dimethyl-2-oxo-1,2,3,4-tetrahydro-quinolin-4-yl)-1H-imidazole-4-carboxylic acid ethyl ester

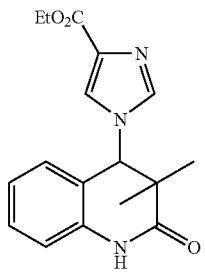

$^1$H NMR (400 MHz, CDCl$_3$) δ ppm 1.14 (s, 3H) 1.31 (s, 3H) 1.35 (t, J=7.07 Hz, 3H) 6.96 (d, J=7.83 Hz, 1H) 7.03-7.11 (m, 1H) 7.17 (d, J=7.58 Hz, 1H) 7.31-7.40 (m, 1H) 7.49 (d, J=1.52 Hz, 1H) 7.54 (d, J=1.52 Hz, 1H) 8.50 (br. s., 4H). $^{13}$C NMR (101 MHz, CDCl$_3$) δ ppm 14.39, 20.13, 24.96, 43.12, 60.70, 64.72, 116.01, 120.11, 123.49, 124.14, 129.19, 130.63, 134.99, 136.14, 137.48, 162.66, 173.08, HRMS (ESI): calculated for C$_{17}$H$_{19}$N$_3$O$_3$: 314.1505. Found: 314.1496.

3-(6-Fluoro-3,3-dimethyl-2-oxo-1,2,3,4-tetrahydro-quinolin-4-yl)-3H-imidazole-4-carboxylic acid methyl ester

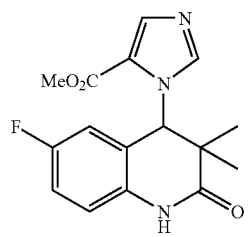

$^1$H NMR (400.3 MHz, CDCl$_3$): δ 9.59 (brs, 1H), 7.76 (s, 1H), 7.56 (s, 1H), 7.07-6.94 (m, 3H), 6.48 (s, 1H), 3.93 (s, 3H), 1.33 (s, 3H), 1.10 (s, 3H). MS (ESI): calculated for: C$_{16}$H$_{16}$FN$_3$O$_3$: 317.3. Found (M+1): 318.

1-(6-Fluoro-3,3-dimethyl-2-oxo-1,2,3,4-tetrahydro-quinolin-4-yl)-1H-imidazole-4-carboxylic acid methyl ester

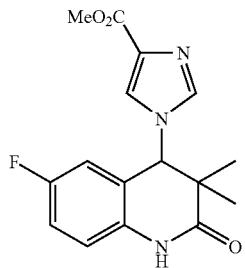

$^1$H NMR (400.3 MHz, CDCl$_3$): δ 9.79 (brs, 1H), 7.63 (s, 1H), 7.54 (s, 1H), 7.09-6.91 (m, 3H), 4.99 (s, 1H), 3.86 (s, 3H), 1.32 (s, 3H), 1.14 (s, 3H). MS (ESI): calculated for: C$_{16}$H$_{16}$FN$_3$O$_3$: 317.3. Found (M+1): 318.2.

1-(6-Fluoro-3,3-dimethyl-2-oxo-1,2,3,4-tetrahydro-quinolin-4-yl)-1H-imidazole-4-carboxylic acid ethyl ester

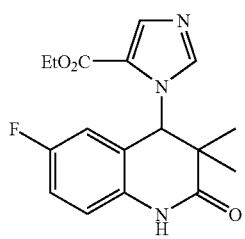

$^1$H NMR (400.3 MHz, CDCl$_3$): δ 9.41 (brs, 1H), 7.75 (s, 1H), 7.55 (s, 1H), 7.06-6.93 (m, 3H), 6.50 (s, 1H), 4.385 (q, J=8 Hz, 2H), 1.42 (t, J=8 Hz, 3H), 1.33 (s, 3H), 1.10 (s, 3H). MS (ESI): calculated for: C$_{17}$H$_{18}$FN$_3$O$_3$: 331.4. Found (M+1): 332.

3-(7-Fluoro-3,3-dimethyl-2-oxo-1,2,3,4-tetrahydro-quinolin-4-yl)-3H-imidazole-4-carboxylic acid methyl ester

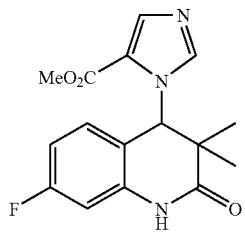

$^1$H NMR (400.3 MHz, CDCl$_3$): δ 9.21 (brs, 1H), 7.68 (s, 1H), 7.49 (s, 1H), 7.23-7.19 (m, 1H), 6.69-6.63 (m, 2H), 6.41 (s, 1H), 3.85 (s, 3H), 1.27 (s, 3H), 1.01 (s, 3H). $^{19}$FNMR (376.64 MHz, CDCl$_3$): −109.55. MS (ESI): calculated for: C$_{16}$H$_{16}$FN$_3$O$_3$: 317.3. Found (M+1): 318.05.

7-Fluoro-3,3-dimethyl-4-(5-methyl-imidazol-1-yl)-3,4-dihydro-1H-quinolin-2-one

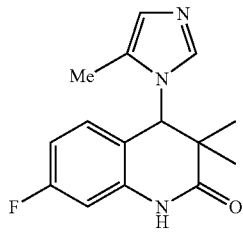

$^1$H NMR (400.3 MHz, CDCl$_3$): δ ppm 1.10 (s, 3 H) 1.30 (s, 3 H) 2.33 (s, 3 H) 4.90 (s, 1 H) 6.67 (dd, J=9.09, 2.40 Hz, 1 H) 6.71-6.81 (m, 1 H) 6.85 (s, 1 H) 7.03 (dd, J=8.34, 5.68 Hz, 1 H) 7.48 (s, 1 H) 8.20 (br. s., 1 H).
MS (ESI): calculated for: C$_{15}$H$_{16}$FN$_3$O: 273.1277. Found: 273.1277.

Example 2

3-(1,3,3-Trimethyl-2,2-dioxo-1,2,3,4-tetrahydro-benzo[c][1,2]thiazin-4-yl)-3H-imidazole-4-carboxylic acid methyl ester

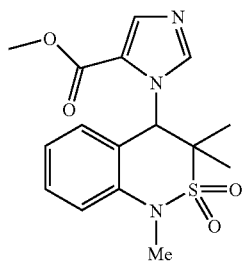

Step A. 1,3,3-Trimethyl-2,2-dioxo-2,3-dihydro-1H-benzo[c][1,2]thiazin-4-one

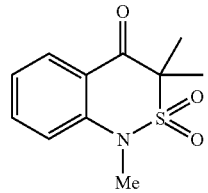

Iodomethane (187 ul, 426 mg, 3 mmol) is added dropwise to a suspension of 2,2-Dioxo-1-methyl-2,1-benzothiazin-4(3H)-one ([CAS: 7117-31-9], 220 mg, 1 mmol), K$_2$CO$_3$ (1.38 g, 10 mmol) in 3 mL of dry DMF at room temperature. The resulting mixture is stirred at 60° C. After 2 h, the reaction mixture is filtered, and washed with ethyl acetate (20 mL). The combined solution is concentrated and the residue is purified by flash column (ethyl acetate-heptane v/v 10%) and gives the title compound as white solid (190 mg).

Step B. 1,3,3-Trimethyl-2,2-dioxo-1,2,3,4-tetrahydro-benzo[c][1,2]thiazin-4-ol

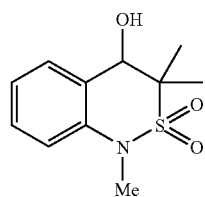

NaBH4 (45 mg, 1.2 mmol) is added to a solution of 1,3,3-Trimethyl-2,2-dioxo-2,3-dihydro-1H-benzo[c][1,2]thiazin-4-one (190 mg, 0.8 mmol) in 15 mL of EtOH at 0° C. The resulting mixture is stirred at this temperature for overnight. The reaction is quenched by HCl (1M), and extracted with ethyl acetate (15 mL×3). The combined extracts are dried over anhydrous Na2SO4. After filtration and concentration, the residue is purified by flash column and yields the title compound as oil (193 mg).

Step C. 3-(1,3,3-Trimethyl-2,2-dioxo-1,2,3,4-tetrahydro-benzo[c][1,2]thiazin-4-yl)-3H-imidazole-4-carboxylic acid methyl ester The title compound is yielded by the reaction of 1,3,3-Trimethyl-2,2-dioxo-1,2,3,4-tetrahydro-benzo[c][1,2]thiazin-4-ol and 3H-Imidazole-4-carboxylic acid methyl ester via the general mitsunobu reaction protocol.

$^1$H NMR (400.3 MHz, CDCl$_3$): δ 7.89 (s, 1H), 7.75 (s, 1H), 7.42 (t, J=8.0 Hz, 1H), 7.10-7.05 (m, 3H), 6.81 (d, J=8.0 Hz, 1H), 3.96 (s, 3H), 3.49 (s, 3H), 1.58 (s, 3H), 1.37 (s, 3H). MS (ESI): calculated for: $C_{16}H_{19}N_3O_4S$: 349.4. Found (M+1): 350.3.

Example 3

3,3-Dimethyl-4-[5-(3-methyl-[1,2,4]oxadiazol-5-yl)-imidazol-1-yl]-3,4-dihydro-1H-quinolin-2-one

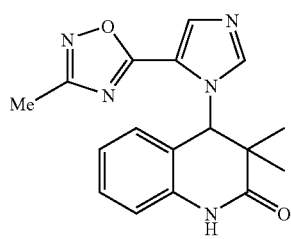

N-hydroxy-acetamidine (62 mg, 0.84 mmol) is added to a suspension of 3 Å molecular sieves in anhydrous THF (2 mL). After 20 min, NaH (60% in oil, 37 mg, 0.92 mmol) is added. The resulting suspension is stirred for 40 min and a solution of 3-(3,3-Dimethyl-2-oxo-1,2,3,4-tetrahydro-quinolin-4-yl)-3H-imidazole-4-carboxylic acid methyl ester (100 mg, 0.34 mmol) in THF (dry, 1 mL) is added. The resulting mixture is refluxed for 1 h. The solvent is removed under vacuum and the residue is purified by silca gel chromatography (mobile phase 0 to 40% ethyl acetate-heptane v/v), and gives the title compound (74 mg).

$^1$H NMR (400.3 MHz, CDCl$_3$): δ ppm 1.00 (s, 3 H) 1.29 (s, 3 H) 2.45 (s, 3 H) 6.53 (s, 1 H) 6.85 (d, J=8.84 Hz, 1 H) 6.98 (t, J=8.08 Hz, 1 H) 7.22 (d, J=7.58 Hz, 1 H) 7.25-7.35 (m, 1 H) 7.57 (s, 1 H) 7.83 (s, 1 H) 7.97 (br. s., 1 H). MS (ESI): calculated for: $C_{17}H_{17}N_5O_2$: 323.1382. Found: 323.1382.

Example 4

3-(1,3,3-Trimethyl-2-oxo-1,2,3,4-tetrahydro-quinolin-4-yl)-3H-imidazole-4-carboxylic acid methyl ester

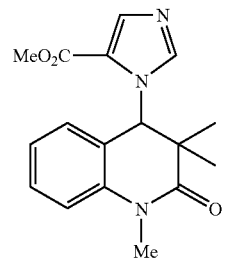

Step A. 3,3-Dimethyl-1H-quinoline-2,4-dione

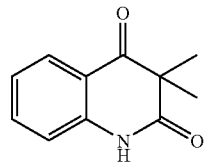

A mixture of 4-Hydroxy-3,3-dimethyl-3,4-dihydro-1H-quinolin-2-one (1.0 g, 5.2 mmol) and MnO$_2$ (4.5 g, 52 mmol) in DMF-CH$_2$Cl$_2$ (10%, v/v, 20 mL) is heat to reflux for overnight (~16 h). The insoluble material is removed by filtration through a pad of celite (~1 cm), and washed with CH$_2$Cl$_2$. The combined solution is concentrated under vacuum, and yields the title compound as colorless solid (675 mg, yield 69%).

Step B. 1,3,3-Trimethyl-1H-quinoline-2,4-dione

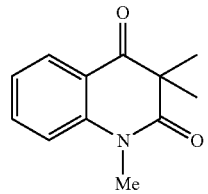

NaH (95% in mineral oil, 42 mg, 1.75 mmol) is added carefully to a solution of 3,3-dimethyl-1H-quinoline-2,4-dione (300 mg, 1.58 mmol) in anhydrous THF (10 mL) at 0° C. After 20 min, MeI (269 mg, 1.89 mmol) is added. The resulting mixture is stirred for overnight (~16 h) at room temperature. Saturated NH$_4$Cl solution is added, the mixture is extracted with ether (20 mL×3). The combined extracts are washed with brine, and dried over anhydrous $Na_2SO_4$. After concentration, the title compound is yielded (300 mg, 93% yield).

Step C. 4-Hydroxy-1,3,3-trimethyl-3,4-dihydro-1H-quinolin-2-one

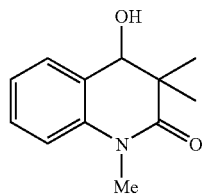

$NaBH_4$ (excess amount) is added to a solution of 1,3,3-Trimethyl-1H-quinoline-2,4-dione (330 mg, 1.62 mmol) in EtOH (8 mL) at 0° C. The resulting mixture is slowly warmed up to room temperature. After 1 h, HCl (10%, 3 mL) is added dropwise. The solvent is removed under vacuum, the residue is dissolved into ether and washed with water, brine, and dried over anhydrous $Na_2SO_4$. After concentration, the title compound is yielded (275 mg, 82% yield).

Step D. 3-(1,3,3-Trimethyl-2-oxo-1,2,3,4-tetrahydro-quinolin-4-yl)-3H-imidazole-4-carboxylic acid methyl ester The title compound is prepared by using the general mitsunobu reaction protocol described in example 1.

$^1$H NMR (400.3 MHz, $CDCl_3$): δ 7.72 (s, 1H), 7.41 (t, J=8 Hz 1H), 7.32 (s, 1H), 7.31 (d, J=8.0 Hz, 1H), 7.12-7.05 (m, 2H), 6.43 (s, 1H), 3.91 (s, 3H), 3.49 (s, 3H), 1.24 (s, 3H), 1.10 (s, 3H). $^{13}$C NMR (100.6 MHz, $CDCl_3$): δ 172.67, 161.55, 139.96, 139.37, 137.62, 130.23, 129.92, 123.76, 122.94, 122.22, 115.17, 59.63, 51.66, 43.52, 30.09, 25.25, 20.18. HRMS (ESI): calculated for $C_{17}H_{19}N_3O_3$: 314.1505. Found: 314.1510.

Example 5

4-(5-Hydroxymethyl-imidazol-1-yl)-3,3-dimethyl-3,4-dihydro-1H-quinolin-2-one

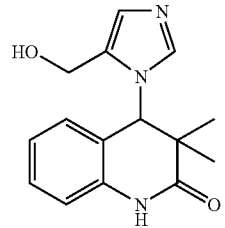

A solution of $LiAlH_4$ (1 M in ether, 1.98 mL, 1.98 mmol) is added dropwise to a solution of 3-(3,3-Dimethyl-2-oxo-1,2,3,4-tetrahydro-quinolin-4-yl)-3H-imidazole-4-carboxylic acid ethyl ester (621 mg, 1.98 mmol) in THF (10 mL) at −10° C. After 4 h at this temperature, the reaction is quenched by the addition of water (0.3 mL), NaOH solution (15%, 0.3 mL) and water (1 mL). The resulting mixture is filtered, and the solid is washed by ether (10 mL×3). The combined solution is concentrated under vacuum, and the residue is purified by reverse phase HPLC (5% to 40% acetonitrile/water with 0.1% $NH_4OH$ over 15 min) to give the title compound (445 mg). $^1$H NMR (400.3 MHz, MeOD): δ 7.43 (d, J=8.0 Hz, 1H) 7.39 (s, 1H), 7.35 (t, J=8 Hz 1H), 7.09-7.03 (m, 2H), 6.91 (s, 1H), 5.39 (s, 1H), 4.72 (d, J=8.0 Hz, 2H) 1.30 (s, 3H), 1.05 (s, 3H), $^{13}$C NMR (100.6 MHz, MeOD): δ 175.93, 138.02, 136.50, 133.43, 131.20, 130.68, 127.52, 124.80, 123.29, 117.07, 61.88, 54.40, 25.68, 19.97. HRMS: calculated for $C_{15}H_{17}N_3O_2$: 272.1399. Found: 272.1407.

Resolution of the enantiomers is achieved by chiral HPLC using the ChiralPak IA column with a 25% EtOH/Heptane as mobile phase to give enantiomers with retention time $t_r$=8.9 min and $t_r$=18 min.

The following compound can be prepared by employing similar procedure.

5-Chloro-4-(5-hydroxymethyl-imidazol-1-yl)-3,3-dimethyl-3,4-dihydro-1H-quinolin-2-one

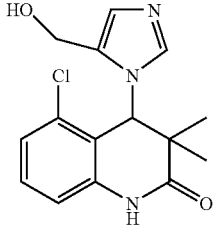

$^1$H NMR (400.3 MHz, MeOD): δ 1.08 (s, 3 H) 1.27 (s, 3 H) 4.71-4.81 (m, 1 H) 4.85-4.97 (m, 1 H) 5.54 (s, 1 H) 6.89 (s, 1 H) 7.00 (d, J=8.08 Hz, 1 H) 7.15 (d, J=8.08 Hz, 1 H) 7.32 (s, 1 H) 7.36 (t, J=8.08 Hz, 1 H). HRMS: calculated for $C_{15}H_{16}ClN_3O_2$: 305.0931. Found: 305.0931.

Example 6

4-Imidazol-1-yl-3,3-dimethyl-3,4-dihydro-1H-quinolin-2-one

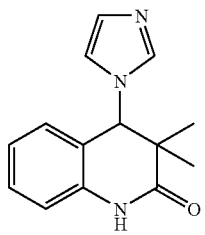

A solution of 4-Hydroxy-3,3-dimethyl-3,4-dihydro-1H-quinolin-2-one (2.0 g, 10.5 mmol), CDI (2.60 g, 15.8 mmol) in 35 mL of acetonitrile is heated to reflux. After 3 h, the solvent is removed under vacuum. The residue is taken up in $CH_2Cl_2$ and washed with water, and dried over anhydrous $Na_2SO_4$. After concentration, the residue is purified by flash column (0 to 3% MeOH/DCM) and Yields 1.38 g of title compound as colorless solid (yield, 55%).

$^1$H NMR (400.3 MHz, MeOD): δ 7.70 (s, 1H), 7.37 (t, J=8 Hz 1H), 7.31 (d, J=8.0 Hz, 1H), 7.10-7.03 (m, 2H), 6.95 (s, 2H), 5.30 (s, 1H), 1.26 (s, 3H), 1.02 (s, 3H), $^{13}$C NMR (100.6 MHz, MeOD): δ 175.95, 138.30, 138.00, 131.27, 130.53, 129.90, 124.83, 122.57, 118.66, 116.95, 64.62, 44.05, 25.23, 20.17. HRMS (ESI): calculated for $C_{14}H_{15}N_3O$: 242.1293. Found: 242.1288.

Resolution of the enantiomers is achieved by chiral HPLC using the ChiralPak AS-H column with a 10% EtOH/Heptane as mobile phase to give enantiomers with retention time $t_r$=18.45 min and $t_r$=22.50 min.

Following compounds can be prepared by the similar procedure.

7-methoxy-4-Imidazol-1-yl-3,3-dimethyl-3,4-dihydro-1H-quinolin-2-one

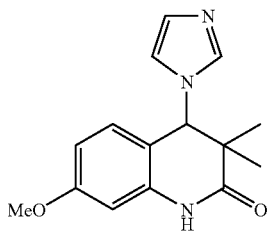

$^1$H NMR (400 MHz, CDCl$_3$) ppm 1.09 (s, 3 H) 1.29 (s, 3 H) 3.80 (s, 3 H) 4.89 (s, 1 H) 6.45 (brs., 1 H) 6.57 (d, 1 H) 6.81 (s, 1 H) 7.02 (s, 1 H) 7.08 (d, J=8.34 Hz, 1 H) 7.53 (s, 1 H). $^{13}$C NMR (101 MHz, CDCl$_3$) ppm 20.14, 25.12, 43.39, 55.49, 63.72, 101.52, 109.17, 113.35, 117.29, 130.11, 130.45, 136.63, 137.37, 160.97, 174.14, HRMS (ESI): calculated for C$_{15}$H$_{17}$N$_3$O$_2$: 271.1320. Found: 271.1365.

Resolution of the enantiomers is achieved by chiral HPLC using the ChiralPak IA column with a 60% EtOH/Heptane as mobile phase to give enantiomers with retention time t$_r$=11.5 min and t$_r$=25.5 min.

4-Imidazol-1-yl-1,3,3-trimethyl-3,4-dihydro-1H-quinolin-2-one

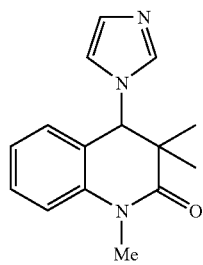

1H NMR (400 MHz, CDCl$_3$) ppm 1.12 (s, 3 H) 1.20 (s, 3 H) 3.48 (s, 3 H) 4.90 (s, 1 H) 6.72 (s, 1 H) 7.02 (s, 1 H) 7.07-7.13 (m, 2 H) 7.14-7.21 (m, 1 H) 7.35-7.44 (m, 1 H) 7.47 (s, 1 H). HRMS: calculated for C$_{15}$H$_{17}$N$_3$O: 255.1371. Found: 255.1372

6-Fluoro-4-imidazol-1-yl-3,3-dimethyl-3,4-dihydro-1H-quinolin-2-one

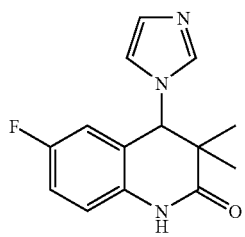

1H NMR (400 MHz, CDCl$_3$) δ ppm 10.1 (brs, 1H), 7.60 (s, 1H), 7.07 (s, 1H), 7.06-6.88 (m, 3H), 6.87 (s, 1H), 4.95 (s, 1H), 1.29 (s, 3H), 1.12 (s, 3H). MS (ESI): calculated for: C$_{14}$H$_{14}$FN$_3$O: 259.3. Found (M+1): 260. Resolution of the enantiomers is achieved by chiral HPLC using the ChiralPak AS-H column with a 10% EtOH/Heptane as mobile phase to give enantiomers with retention time t$_r$=13.46 min and t$_r$=16.55 min.

Example 7

3-(1-Benzoyl-1,2,3,4-tetrahydro-quinolin-4-yl)-3H-imidazole-4-carboxylic acid methyl ester

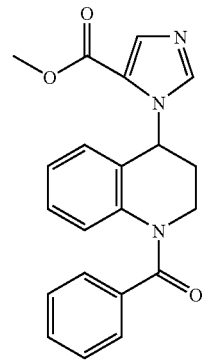

Step A 3-Phenylamino-propionic acid

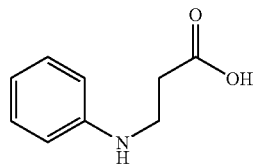

A mixture of 3-phenylamino-propionitrile (5.03 g, 34.4 mmol) in 60 mL of NaOH (10%) solution is heated to reflux. After 1 h, the mixture is cooled and acidified with acetic acid. The resulting solution is subsequently extracted with ethyl acetate and the combined extracts are washed by brine, and dried over anhydrous sodium sulfate. After concentration, the residue is purified by flash chromatography (methanol-dichloromethane), and gives the title compound (4.39 g, 77.7% yield).

Step B 2,3-Dihydro-1H-quinolin-4-one

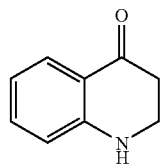

The mixture of 3-phenylamino-propionic acid (1.22 g, 7.39 mmol) in Eaton's reagent (40 mL) is stirred at 70° C. for overnight. The resulting mixture is poured into ice and basified by the slow addition of NaOH (50%) solution. The basified mixture is extracted with ethyl acetate and washed by brine, and dried over anhydrous sodium sulfate. After concentration, the residue is purified by flash chromatography, and gives the title compound (0.5 g, 46.3% yield).

Step C. 1-Benzoyl-2,3-dihydro-1H-quinolin-4-one

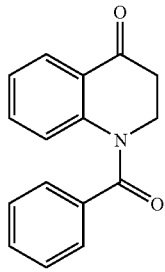

Benzoyl chloride (0.30 ml, 2.58 mmol) is added dropwise to a solution of 2,3-dihydro-1H-quinolin-4-one (260 mg, 1.77 mmol), triethylamine (0.32 ml, 2.30 mmol) and DMAP (10 mg) in $CH_2Cl_2$ at 0° C. The resulting mixture is stirred at room temperature for overnight. Water is added and the mixture is extracted with $CH_2Cl_2$ and washed with brine, dried over anhydrous sodium sulfate. After concentration, a residue is yielded, which is used "as is" for the next reaction without further purification.

Step D (4-Hydroxy-3,4-dihydro-2H-quinolin-1-yl)-phenyl-methanone

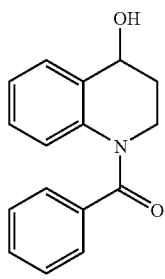

$NaBH_4$ (85 mg, 2.25 mmol) is added to a solution of 1-benzoyl-2,3-dihydro-1H-quinolin-4-one (from step C) in methanol (5 mL) at 0° C. The resulting mixture is stirred at room temperature. After 1 h, the reaction is quenched by 1 N HCl. The solvent is removed under vacuum. The residue is taken up in $CH_2Cl_2$ and washed by brine, and dried over anhydrous sodium sulfate. After concentration, the residue is purified by flash chromatography to give the title compound (380 mg, 84.8% yield for the two steps).

Step E 3-(1-Benzoyl-1,2,3,4-tetrahydro-quinolin-4-yl)-3H-imidazole-4-carboxylic acid methyl ester methyl 4-imidazolecarboxylate (200 mg, 1.59 mmol) and PS-triphenylphosphine (2.15 mmol/g, 0.90 g, 1.94 mmol) are added to a solution of (4-hydroxy-3,4-dihydro-2H-quinolin-1-yl)-phenyl-methanone (380 mg, 1.50 mmol) in THF (20 mL) at room temperature. The resulting mixture is stirred at room temperature for 5 minutes and then cooled to 0° C. DIAD (0.38 mL, 1.96 mmol) is added, and the mixture is slowly warmed up to room temperature. After 3 h, the reaction mixture is filtered to remove resin and washed with ethyl acetate. The combined ethyl acetate solution is washed with brine, and dried with anhydrous sodium sulfate. After concentration, the residue is purified by reverse phase HPLC ($CH_3CN:H_2O=10$ to 80% over 20 mins) to give the title compound: 1H NMR (400 MHz, $CDCl_3$) δ ppm 2.21-2.30 (m, 1 H), 2.52-2.62 (m, 1 H), 3.75-3.82 (m, 1 H), 3.89 (s, 3 H), 4.11-4.18 (m, 1 H), 6.40 (t, J=6.1 Hz, 1 H), 6.94 (d, J=7.6 Hz, 1 H), 7.01-7.09 (m, 3 H), 7.33-7.40 (m, 3 H), 7.40-7.45 (m, 1 H), 7.46-7.50 (m, 2 H), 7.85 (d, J=0.8 Hz, 1 H).

The following compounds can be synthesized in a similar manner:

3-(1-Acetyl-1,2,3,4-tetrahydro-quinolin-4-yl)-3H-imidazole-4-carboxylic acid methyl ester

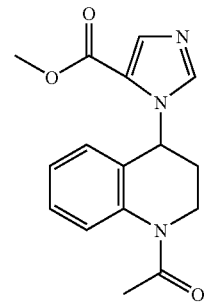

1H NMR (400 MHz, CHLOROFORM-d) δ ppm 2.18-2.28 (m, 1 H), 2.31 (s, 3 H), 2.43-2.54 (m, 1 H), 3.66-3.77 (m, 1 H), 3.86 (s, 3 H), 3.96-4.06 (m, 1 H), 6.26 (t, J=6.2 Hz, 1 H), 6.94 (d, J=7.6 Hz, 1 H), 7.13 (t, J=7.6 Hz, 1 H), 7.28-7.36 (m, 2 H), 7.47 (br. s., 1 H), 7.81 (s, 1 H). HRMS: calcd for $C_{16}H_{18}N_3O_3$: 300.1348, found: m/z 300.1345 (M-H)$^+$

3-(1-Benzenesulfonyl-1,2,3,4-tetrahydro-quinolin-4-yl)-3H-imidazole-4-carboxylic acid methyl ester

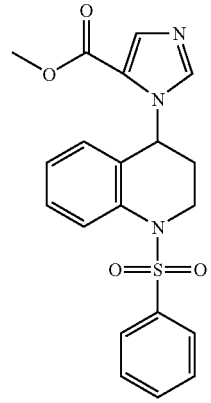

1H NMR (400 MHz, CHLOROFORM-d) δ ppm 1.77-1.87 (m, 1 H), 2.01-2.12 (m, 1 H), 3.72-3.81 (m, 1 H), 3.83 (s, 3 H), 3.96-4.05 (m, 1 H), 6.12 (t, J=6.1 Hz, 1 H), 6.55 (s, 1 H), 6.90 (d, J=7.6 Hz, 1 H), 7.10 (t, J=7.5 Hz, 1 H), 7.31-7.37 (m, 1 H), 7.42-7.48 (m, 2 H), 7.60 (t, J=7.5 Hz, 1 H), 7.64-7.68 (m, 2 H), 7.70 (s, 1 H), 8.01 (d, J=8.3 Hz, 1 H). HRMS: calculated for $C_{20}H_{20}N_3O_4S$: 398.1175. Found: 398.1174.

Resolution of the enantiomers is achieved by chiral HPLC using the ChiralPak IA column with a 40% IPA/Heptane as mobile phase to give enantiomers with retention time $t_r$=14.6 min and $t_r$=19.9 min.

3-[1-(4-Fluoro-benzenesulfonyl)-1,2,3,4-tetrahydro-quinolin-4-yl]-3H-imidazole-4-carboxylic acid methyl ester

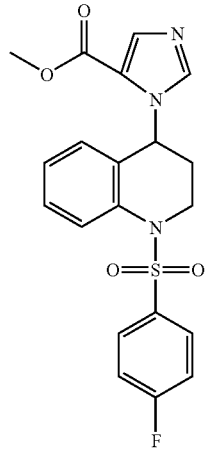

1H NMR (400 MHz, CHLOROFORM-d) δ ppm 1.86-1.96 (m, 1 H), 2.04-2.15 (m, 1 H), 3.62-3.71 (m, 1 H), 3.84 (s, 3 H), 4.07 (dq, J=10.7, 7.0, 3.4 Hz, 1 H), 6.08 (t, J=5.6 Hz, 1 H), 6.76 (s, 1 H), 6.92 (d, J=7.6 Hz, 1 H), 7.08-7.17 (m, 3 H), 7.35 (t, J=8.5 Hz, 1 H), 7.66-7.71 (m, 2 H), 7.73 (s, 1 H), 7.97 (d, J=8.6 Hz, 1 H). HRMS: calculated for $C_{20}H_{19}FN_3O_4S$: 416.1080. Found: 416.1064.

Resolution of the enantiomers is achieved by chiral HPLC using the ChiralPak IA column with a 70% IPA/Heptane as mobile phase to give enantiomers with retention time $t_r$=21.7 min and $t_r$=25.4 min.

Example 8

3-(1-Benzoyl-3,3-dimethyl-1,2,3,4-tetrahydro-quinolin-4-yl)-3H-imidazole-4-carboxylic acid methyl ester

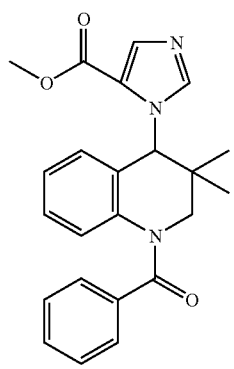

Step A. 1-Benzoyl-3,3-dimethyl-2,3-dihydro-1H-quinolin-4-one

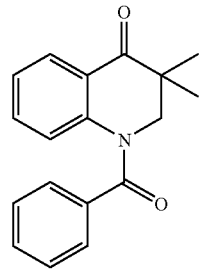

NaH (60% oil suspension, 0.97 g, 24.2 mmol) is added to a solution of 1-benzoyl-2,3-dihydro-1H-quinolin-4-one (2.03 g, 8.09 mmol) in THF (30 mL) at −40° C. After 15 min, CH$_3$I (1.51 mL, 24.2 mmol) is added and the reaction mixture is slowly warmed up to room temperature. After 3.5 h, the reaction is quenched with water and extracted with ethyl acetate. The combined extracts are washed with brine and dried over anhydrous sodium sulfate. After concentration, a crude produce is yielded.

Step B. (4-Hydroxy-3,3-dimethyl-3,4-dihydro-2H-quinolin-1-yl)-phenyl-methanone

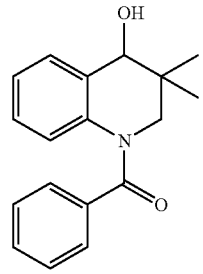

NaBH$_4$ (306 mg, 8.09 mmol) is added to a solution of 1-benzoyl-3,3-dimethyl-2,3-dihydro-1H-quinolin-4-one (crude from step A) in MeOH (10 mL) at 0° C. The resulting mixture is allowed to warm up to room temperature. After 1 h, the reaction is quenched with 1 N HCl, and the solvent is evaporated under vacuum. The residue is taken up in CH$_2$Cl$_2$ and washed with brine, dried over anhydrous sodium sulfate. After concentration, the residue is purified with flash chromatography to the title compound (1.6 g, 70.5% yield for the two steps).

Step C 3-(1-Benzoyl-3,3-dimethyl-1,2,3,4-tetrahydro-quinolin-4-yl)-3H-imidazole-4-carboxylic acid methyl ester methyl 4-imidazolecarboxylate (55 mg, 0.44 mmol), PS-triphenylphosphine (2.15 mmol/g, 0.20 g, 0.43 mmol) are added to a solution of (4-hydroxy-3,3-dimethyl-3,4-dihydro-2H-quinolin-1-yl)-phenyl-methanone (80 mg, 0.28 mmol) in THF (10 mL) at room temperature. The mixture is stirred at room temperature for 5 minutes and then Cooled to 0° C. DIAD (0.083 mL, 0.43 mmol) is added, and then the mixture is stirred at room temperature. After 3 h, the reaction mixture is filtered to remove resin and washed with ethyl acetate. The ethyl acetate solution is washed with brine, and dried over anhydrous sodium sulfate. After concentration, the residue is purified by reverse phase HPLC (CH$_3$CN:H$_2$O=20 to 90% over 20 mins) and yields the title compound: 1H NMR (400 MHz, CHLOROFORM-d) δ ppm 0.74 (s, 3 H), 1.15 (s, 3 H), 3.52 (d, J=13.4 Hz, 1 H), 3.87 (d, J=13.1 Hz, 1 H), 3.92 (s, 3 H), 5.30 (s, 1 H), 6.40 (s, 1 H), 6.95-6.99 (m, 1 H), 7.01-7.06 (m, 1 H), 7.11-7.16 (m, 1 H), 7.28-7.33 (m, 2 H), 7.38-7.44 (m, 2 H), 7.45-7.50 (m, 1 H), 7.52-7.56 (m, 2 H). HRMS: calculated for C$_{23}$H$_{24}$N$_3$O$_3$: 390.1818. Found: 390.1800

The following compounds can be synthesized in a similar manner:

3-[1-(2,2-Dimethyl-propionyl)-3,3-dimethyl-1,2,3,4-tetrahydro-quinolin-4-yl]-3H-imidazole-4-carboxylic acid methyl ester

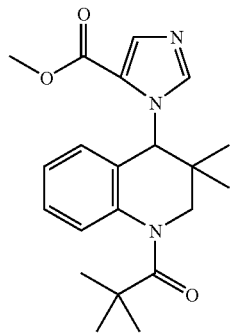

1H NMR (400 MHz, CHLOROFORM-d) δ ppm 0.78 (s, 3 H), 1.12 (s, 3 H), 1.43 (s, 9 H), 3.48 (d, J=13.1 Hz, 1 H), 3.67 (d, J=13.1 Hz, 1 H), 3.92 (s, 3 H), 6.31 (s, 1 H), 6.91 (d, J=7.6 Hz, 1 H), 6.98-7.03 (m, 1 H), 7.24 (s, 1 H), 7.29 (s, 1 H), 7.52 (d, J=8.3 Hz, 1 H), 7.82 (s, 1 H). HRMS: calculated for C$_{21}$H$_{28}$N$_3$O$_3$: 370.2131. Found: 370.2127.

3-[1-(3-Methoxy-benzoyl)-3,3-dimethyl-1,2,3,4-tetrahydro-quinolin-4-yl]-3H-imidazole-4-carboxylic acid methyl ester

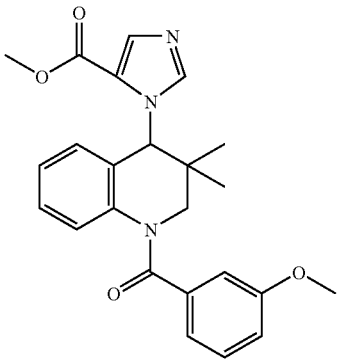

1H NMR (400 MHz, CHLOROFORM-d) δ ppm 0.75 (s, 3 H), 1.14 (s, 3 H), 3.51 (d, J=13.4 Hz, 1 H), 3.83 (s, 3 H), 3.86 (d, J=13.4 Hz, 1 H), 3.93 (s, 3 H), 6.40 (s, 1 H), 6.95-6.99 (m, 1 H), 6.99-7.05 (m, 2 H), 7.06-7.11 (m, 2 H), 7.13-7.19 (m, 1 H), 7.28-7.37 (m, 3 H), 7.82 (s, 1 H).

3-[3,3-Dimethyl-1-(morpholine-4-carbonyl)-1,2,3,4-tetrahydro-quinolin-4-yl]-3H-imidazole-4-carboxylic acid methyl ester

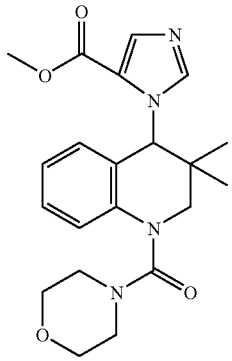

1H NMR (400 MHz, CHLOROFORM-d) δ ppm 0.77 (s, 3 H), 1.13 (s, 3 H), 3.30-3.57 (m, 6 H), 3.67-3.79 (m, 4 H), 3.93 (s, 3 H), 6.31 (s, 1 H), 6.93 (d, J=26.3 Hz, 2 H), 7.20-7.23 (m, 1 H), 7.25 (dd, J=6.4, 1.9 Hz, 1 H), 7.36 (s, 1 H), 7.82 (s, 1 H).

3-(1-Benzenesulfonyl-3,3-dimethyl-1,2,3,4-tetrahydro-quinolin-4-yl)-3H-imidazole-4-carboxylic acid methyl ester

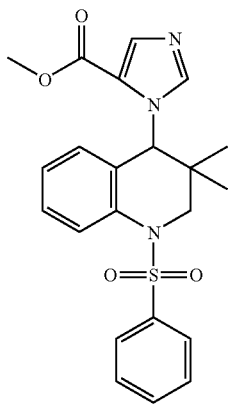

1H NMR (400 MHz, CHLOROFORM-d) δ ppm 0.86 (s, 3 H), 1.16 (s, 3 H), 3.50 (d, J=12.9 Hz, 1 H), 3.90 (s, 3 H), 3.96 (dd, J=12.9, 1.0 Hz, 1 H), 6.27 (s, 1 H), 6.89-7.00 (m, 3 H), 7.20-7.26 (m, 1 H), 7.55-7.60 (m, 2 H), 7.63-7.68 (m, 1 H), 7.74-7.79 (m, 2 H), 7.91-7.95 (m, 2 H). HRMS: calculated for C$_{22}$H$_{24}$N$_3$O$_4$S: 426.1488. Found: 426.1484.

Resolution of the enantiomers is achieved by chiral HPLC using the ChiralPak IA column with a 20% EtOH/Heptane as mobile phase to give enantiomers with retention time t$_r$=12.28 min and t$_r$=19.48 min.

Example 9

[3-(3,3-Dimethyl-1,2,3,4-tetrahydro-quinolin-4-yl)-3H-imidazole-4-yl]-methanol

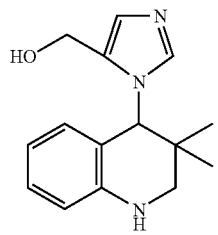

LiAlH$_4$ (26 mg, 0.68 mmol) is carefully added to a solution of 3-(1-benzoyl-3,3-dimethyl-1,2,3,4-tetrahydro-quinolin-4-yl)-3H-imidazole-4-carboxylic acid methyl ester (101 mg, 0.26 mmol) in THF (10 mL) at 0° C. The resulting mixture is warmed up to room temperature. After overnight, NaF and water are added at 0° C. Then the reaction mixture is warmed up to room temperature and stirred until the grey suspension turned to off white color. The mixture is filtered and the filtrate is concentrated and taken up into ethyl acetate and washed with brine, and dried over anhydrous sodium sulfate. After concentration, the residue is purified by flash chromatography and gives the title compound (23 mg, 34.5% yield). 1H NMR (400 MHz, CHLOROFORM-d) δ ppm 0.81 (s, 3 H), 1.08 (s, 3 H), 2.68 (br. s., 1 H), 2.97 (d, J=12.1 Hz, 1 H), 3.19 (d, J=12.1 Hz, 1 H), 4.22 (br. s., 1 H), 4.73 (s, 2 H), 5.11 (s, 1 H), 6.54-6.61 (m, 2 H), 6.87 (s, 1 H), 6.92 (d, J=7.3 Hz, 1 H), 7.08 (t, J=8.3 Hz, 1 H), 7.28 (s, 1 H). HRMS: calculated for C$_{15}$H$_{20}$N$_3$O: 258.1606. Found: 258.1615.

Resolution of the enantiomers is achieved by chiral HPLC using the ChiralPak OD column with a 10% EtOH/Hexane as mobile phase to give enantiomers with retention time t$_r$=21.50 min and t$_r$=26.53 min.

Example 10

[3-(1-Benzyl-3,3-dimethyl-1,2,3,4-tetrahydro-quinolin-4-yl)-3H-imidazole-4-yl]-methanol

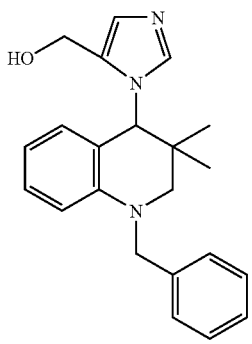

2 drops of HOAc are added to a suspension of [3-(3,3-dimethyl-1,2,3,4-tetrahydro-quinolin-4-yl)-3H-imidazole-4-yl]-methanol (65 mg, 0.25 mmol) in DCE at room temperature. Benzaldehyde (0.1 ml, 1.0 mmol) and NaBH(OAc)$_3$ (152 mg, 0.72 mmol) are added subsequently to reaction mixture. The mixture is stirred at room temperature for overnight. The reaction is quenched with sat. NaHCO$_3$ and extracted with CH$_2$Cl$_2$, washed by brine, dried over anhydrous sodium sulfate. After concentration, the residue is purified by reverse phase HPLC (CH$_3$CN:H$_2$O=20 to 90% over 20 mins) to the title compound: 1H NMR (400 MHz, CHLOROFORM-d) δ ppm 0.81 (s, 3 H), 1.09 (s, 3 H), 2.99 (dd, J=12.3, 1.4 Hz, 1 H), 3.25 (d, J=12.4 Hz, 1 H), 3.41 (br. s., 1 H), 4.55 (d, J=16.7 Hz, 1 H), 4.62 (d, J=16.9 Hz, 1H), 4.69 (s, 2 H), 5.19 (s, 1 H), 6.55 (t, J=7.5 Hz, 1 H), 6.69 (d, J=8.3 Hz, 1 H), 6.76 (s, 1 H), 6.98 (d, J=7.6 Hz, 1 H), 7.09 (s, 1 H), 7.22 (s, 1 H), 7.27-7.38 (m, 5 H).

Resolution of the enantiomers is achieved by chiral HPLC using ChiralPak OD-H column with a 10% Heptane/Isopropanol as mobile phase to give enantiomers with retention time t$_r$=21.4 min and t$_r$=25.5 min.

The following compound can be synthesized in a similar manner:

[3-(1-Butyl-3,3-dimethyl-1,2,3,4-tetrahydro-quinolin-4-yl)-3H-imidazole-4-yl]-methanol

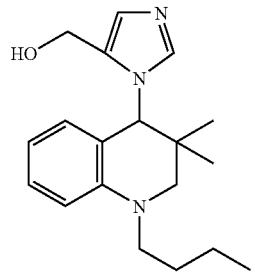

1H NMR (400 MHz, CHLOROFORM-d) δ ppm 0.79 (s, 3 H), 1.00 (t, J=7.3 Hz, 3 H), 1.03 (s, 3 H), 1.36-1.47 (m, 2 H), 1.59-1.69 (m, 2 H), 2.87 (dd, J=12.4, 1.5 Hz, 1 H), 3.22 (d, 1 H), 3.26-3.45 (m, 3 H), 4.68 (s, 2 H), 5.10 (s, 1 H), 6.50 (t, J=7.2 Hz, 1 H), 6.68 (d, J=8.3 Hz, 1 H), 6.73 (s, 1 H), 6.97 (dd, J=7.3, 1.3 Hz, 1 H), 7.11-7.17 (m, 1 H), 7.18 (s, 1 H).

[3-(1,3,3-Trimethyl-1,2,3,4-tetrahydro-quinolin-4-yl)-3H-imidazol-4-yl]-methanol

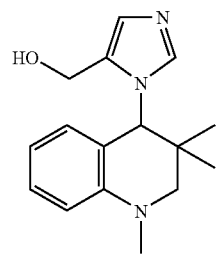

1H NMR (400 MHz, CHLOROFORM-d) δ ppm 0.81 (s, 3H), 1.06 (s, 3H), 2.48 (br. s., 1H), 2.89 (dd, J=12.1, 1.5 Hz, 1H), 3.04 (s, 3H), 3.19 (d, J=12.4 Hz, 1H), 4.71 (s, 2H), 5.13 (s, 1H), 6.58 (t, J=7.8 Hz, 1H), 6.70 (d, J=8.3 Hz, 1H), 6.84 (s, 1H), 6.94 (d, J=6.6 Hz, 1H), 7.15-7.24 (m, 2H); HRMS calcd for C$_{16}$H$_{20}$N$_3$O: 270.1606. found 270.1617.

Example 11

1-[4-(5-Hydroxymethyl-imidazol-1-yl)-3,3-dimethyl-3,4-dihydro-2H-quinolin-1-yl]-2-phenyl-ethanone

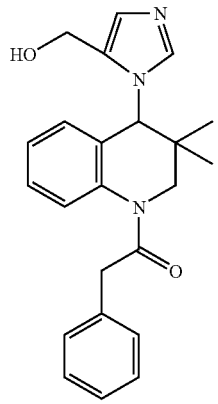

Step A. 4-[5-(tert-Butyl-diphenyl-silanyloxymethyl)-imidazol-1-yl]-3,3-dimethyl-1,2,3,4-tetrahydroquinoline

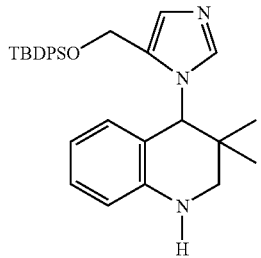

Imidazole (23 mg, 0.24 mmol) and followed by tert-butylchlorodiphenylsilane (0.063 mL, 0.24 mmol) are added to a suspension of [3-(3,3-dimethyl-1,2,3,4-tetrahydro-quinolin-4-yl)-3H-imidazole-4-yl]-methanol (60 mg, 0.23 mmol) in $CH_2Cl_2$ (2 mL) at 0° C. The resulting mixture is warmed up to room temperature. After 1 h, the reaction is quenched by sat. $NH_4Cl$ and extracted with $CH_2Cl_2$, washed with brine, and dried over anhydrous sodium sulfate. After concentration, the residue is purified by flash chromatography to the title compound (105 mg, 90.5% yield).

Step B. 1-{4-[5-(tert-butyl-diphenyl-silanyloxymethyl)-imidazol-1-yl]-3,3-dimethyl-3,4-dihydro-2H-quinolin-1-yl}-2-phenyl-ethanone

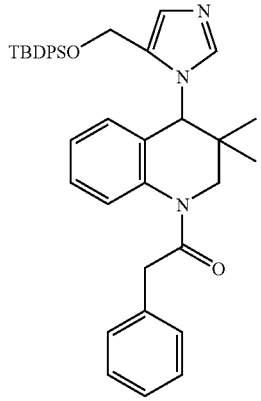

Phenylacetyl chloride (0.08 ml, 0.60 mmol) is added to a solution of 4-[5-(tert-butyl-diphenyl-silanyloxymethyl)-imidazol-1-yl]-3,3-dimethyl-1,2,3,4-tetrahydro-quinoline (105 mg, 0.21 mmol), triethylamine (0.082 ml, 0.59 mmol) and DMAP (5 mg) in $CH_2Cl_2$ at 0° C. The mixture is stirred at room temperature for overnight. The reaction is quenched with water and extracted with $CH_2Cl_2$ and washed with brine; dried over anhydrous sodium sulfate and concentrated to give the crude mixture.

$K_2CO_3$ (65 mg, 0.47 mmol) is added to the above crude mixture in MeOH (10 mL) at 0° C. The resulting mixture is stirred at room temperature. After 3 h, the mixture is concentrated and dissolved into ethyl acetate and washed with brine; dried with anhydrous sodium sulfate and concentrated to give the crude product (115 mg).

Step C. 1-[4-(5-Hydroxymethyl-imidazol-1-yl)-3,3-dimethyl-3,4-dihydro-2H-quinolin-1-yl]-2-phenyl-ethanone HOAc (0.05 mL, 0.88 mmol) and TBAF (0.3 mL, 0.37 mmol) are added to a solution of 1-{4-[5-(tert-butyl-diphenyl-silanyloxymethyl)-imidazol-1-yl]-3,3-dimethyl-3,4-dihydro-2H-quinolin-1-yl}-2-phenyl-ethanone (115 mg) in THF (6 mL) at room temperature. The mixture is stirred at room temperature. In the next 4 h, TBAF (0.3 mL×2) are added and the mixture is stirred at room temperature for overnight. The reaction is adjusted by sat. $NaHCO_3$ to basic and extracted into ethyl acetate and washed with brine; dried with anhydrous sodium sulfate and concentrated to give the crude compound, which is purified by reverse phase HPLC ($CH_3CN:H_2O$=10 to 80% over 20 mins) to the title compound: 1H NMR (400 MHz, CHLOROFORM-d) δ ppm 0.73 (s, 3 H), 0.97 (s, 3 H), 3.53 (br. s., 1H), 3.65 (d, J=13.1 Hz, 1 H), 3.83 (d, J=13.1 Hz, 1 H), 4.00 (s, 2 H), 4.70 (dd, 2 H), 5.30 (s, 1 H), 6.89-6.95 (m, 2 H), 7.03 (t, J=7.5 Hz, 1 H), 7.10 (s, 1 H), 7.24-7.37 (m, 6 H), 7.61 (br. s., 1 H).

Example 12

4-Imidazol-1-yl-3,3-dimethyl-1,2,3,4-tetrahydroquinoline

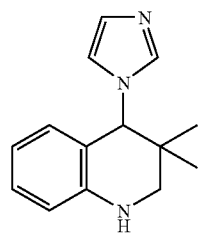

To a solution of 4-imidazol-1-yl-3,3-dimethyl-3,4-dihydro-1H-quinolin-2-one (80 mg, 0.332 mmol) in THF (3 mL) at room temperature is added $BH_3$-THF (3.3 mL, 1.0 M solution) and the mixture is stirred at room temperature for 1 h. To the reaction mixture is added 6N HCl until no hydrogen gas evolves from the solution. The reaction mixture is stirred for 2 h at room temperature and is added aqueous 10% NaOH to adjust PH=12 and then the mixture is extracted into $CH_2Cl_2$ and washed by brine; dried with anhydrous sodium sulfate and concentrated to give the crude compound. Reverse phase HPLC ($CH_3CN:H_2O$=20 to 90% over 20 mins) purification gives the title compound: 1H NMR (400 MHz, CHLORO- FORM-d) δ ppm 0.85 (s, 3 H), 1.06 (s, 3 H), 2.92-3.00 (m, 1 H), 3.12 (d, J=11.9 Hz, 1 H), 4.18 (br. s., 1 H), 4.78 (s, 1 H), 6.57-6.66 (m, 2 H), 6.80 (s, 1 H), 6.86 (d, J=7.1 Hz, 1 H), 7.02 (s, 1 H), 7.07-7.14 (m, 1 H), 7.47 (s, 1 H).

We claim:

1. A compound of formula (I):

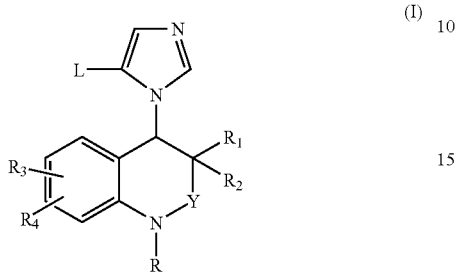

wherein Y is —C(O)—; L is hydrogen, cyano, halogen, $(C_1-C_7)$ haloalkyl, $(C_3-C_7)$ cycloalkyl, $(C_3-C_7)$ alkyl-O—C(O)—, or $(C_1-C_7)$ alkyl that is optionally substituted by one or two hydroxyl groups; $R_1$ and $R_2$ are independently hydrogen or $(C_1-C_7)$ alkyl; $R_3$ and $R_4$ are independently hydrogen, halogen, $(C_1-C7)$ alkoxy; R is hydrogen, $(C_1-C_7)$ alkyl, $(C_1-C_7)$ haloalkyl, or $(C_3-C_7)$ cycloalkyl, (4-9)-membered heterocyclyl; or a pharmaceutically acceptable salt thereof; or an optical isomer thereof; or a mixture of optical isomers.

2. A method of treating a disorder or a disease in a subject mediated by aldosterone synthase, comprising: administering to the subject a therapeutically effective amount of the compound according to claim 1, wherein the disorder or the disease is selected from hypokalemia, hypertension, congestive heart failure, renal failure, restenosis, atherosclerosis, syndrome X, obesity post-myocardial infarction, coronary heart diseases, fibrosis and remodeling following hypertension and endothelial dysfunction.

3. A pharmaceutical composition, comprising:
a therapeutically effective amount of the compound of claim 1 and one or more pharmaceutically acceptable carriers.

4. A pharmaceutical composition, comprising:
a therapeutically effective amount of the compound according to claim 1 and one or more therapeutically active agents selected from (i) HMG-Co-A reductase inhibitor or a pharmaceutically acceptable salt thereof; (ii) angiotensin II receptor antagonist or a pharmaceutically acceptable salt thereof; (iii) angiotensin converting enzyme (ACE) Inhibitor or a pharmaceutically acceptable salt thereof; (iv) calcium channel blocker (CCB) or a pharmaceutically acceptable salt thereof; (v) dual angiotensin converting enzyme/neutral endopeptidase (ACE/NEP) inhibitor or a pharmaceutically acceptable salt thereof; (vi) endothelin antagonist or a pharmaceutically acceptable salt thereof; (vii) renin inhibitor or a pharmaceutically acceptable salt thereof; (viii) diuretic or a pharmaceutically acceptable salt thereof; (ix) an ApoA-I mimic; (x) an anti-diabetic agent; (xi) an obesity-reducing agent; (xii) an aldosterone receptor blocker; (xiii) an endothelin receptor blocker; and (xiv) CETP inhibitor.

5. The compound of claim 1, wherein Y is —C(O)—; L is hydrogen; $R_1$ and $R_2$ are each methyl; one of $R_3$ and $R_4$ is hydrogen and the other one is hydrogen or halogen; and R is hydrogen.

6. The compound of claim 1, wherein the compound is 4-Imidazol-1-yl-3, 3-dimethyl-3,4-dihydro-1H-quinolin-2-one.

7. The compound of claim 1, wherein the compound is 6-Fluoro-4-imidazol-1-yl-3,3-dimethyl-3,4-dihydro-1H-quinolin-2-one.

* * * * *